(12) United States Patent
Scheller et al.

(10) Patent No.: US 12,201,317 B2
(45) Date of Patent: Jan. 21, 2025

(54) IRRIGATION SYSTEM FOR AN ULTRASONIC SURGICAL HANDPIECE

(71) Applicant: Kogent Surgical, LLC, Chesterfield, MO (US)

(72) Inventors: Gregg D Scheller, Wildwood, MO (US); Steven J Apperson, Ballwin, MO (US); Johanna L Bryan, Chesterfield, MO (US); David G Wuchinich, Bronx, NY (US)

(73) Assignee: Kogent Surgical, LLC, Chesterfield, MO (US)

( * ) Notice: Subject to any disclaimer, the term of this patent is extended or adjusted under 35 U.S.C. 154(b) by 964 days.

(21) Appl. No.: 16/592,918

(22) Filed: Oct. 4, 2019

(65) Prior Publication Data
US 2020/0108186 A1    Apr. 9, 2020

Related U.S. Application Data

(60) Provisional application No. 62/741,606, filed on Oct. 5, 2018.

(51) Int. Cl.
*A61B 17/32* (2006.01)
*A61M 1/00* (2006.01)
*A61M 3/02* (2006.01)

(52) U.S. Cl.
CPC ..... *A61B 17/320068* (2013.01); *A61M 1/772* (2021.05); *A61M 3/0254* (2013.01); *A61B 2017/32007* (2017.08); *A61M 1/774* (2021.05)

(58) Field of Classification Search
CPC ............... A61M 1/774; A61M 1/0062; A61B 17/320068; A61B 2217/007; A61B 2017/32007; A61B 8/4477; A61B 2017/00106; A61B 2017/320084
See application file for complete search history.

(56) References Cited

U.S. PATENT DOCUMENTS

| 3,805,787 A | * | 4/1974 | Banko | A61F 9/00745 |
| | | | | 606/171 |
| 3,990,452 A | * | 11/1976 | Murry | A61F 9/00745 |
| | | | | 606/169 |
| 4,425,115 A | * | 1/1984 | Wuchinich | A61B 17/22004 |
| | | | | 606/169 |

(Continued)

*Primary Examiner* — Nilay J Shah
(74) *Attorney, Agent, or Firm* — Jay J. Hoette; The Small Patent Law Group, LLC

(57) ABSTRACT

An ultrasonic surgical handpiece includes a motor having a transducer assembly along a central axis of the surgical handpiece. The motor is configured for operative connection to a power source. A surgical attachment has a proximal end detachably connected to the motor and a distal end defining a working plane for engagement with biological tissue. A housing has a housing distal end, a housing proximal end, and a cavity configured to receive the motor and the surgical attachment. An irrigation path of the housing is configured to communicate irrigation fluid. The irrigation path has an inlet proximate the housing proximal end operatively connected to an irrigation fluid source, and an outlet proximate to the working plane. The irrigation path is separated from the housing cavity to prevent contact between the irrigation fluid and an operational portion of the surgical attachment.

30 Claims, 17 Drawing Sheets

(56) References Cited

U.S. PATENT DOCUMENTS

| | | | | |
|---|---|---|---|---|
| 4,428,748 | A * | 1/1984 | Peyman | A61F 9/00745 |
| | | | | 433/119 |
| 4,516,398 | A * | 5/1985 | Wuchinich | A61M 1/85 |
| | | | | 604/35 |
| 5,254,082 | A * | 10/1993 | Takase | A61B 17/320068 |
| | | | | 606/107 |
| 5,413,556 | A * | 5/1995 | Whittingham | A61F 9/00745 |
| | | | | 606/107 |
| 5,486,162 | A * | 1/1996 | Brumbach | A61F 9/00745 |
| | | | | 604/22 |
| 5,562,609 | A * | 10/1996 | Brumbach | A61B 17/320068 |
| | | | | 601/3 |
| 5,562,610 | A * | 10/1996 | Brumbach | A61B 17/320068 |
| | | | | 601/3 |
| 5,807,310 | A | 9/1998 | Hood | |
| 6,171,300 | B1 * | 1/2001 | Adams | A61B 17/1644 |
| | | | | 433/104 |
| 6,342,061 | B1 | 1/2002 | Kauker | |
| 7,717,931 | B2 | 5/2010 | Himes | |
| 8,475,481 | B2 | 7/2013 | Himes | |
| 8,836,200 | B2 | 9/2014 | Young | |
| 9,820,834 | B2 | 11/2017 | Maxwell | |
| 10,052,432 | B2 | 8/2018 | Dexter | |
| 2005/0245898 | A1 * | 11/2005 | Wright | A61M 1/774 |
| | | | | 604/533 |
| 2008/0015490 | A1 | 1/2008 | Hershberger | |
| 2014/0356808 | A1 | 12/2014 | Pond | |

\* cited by examiner

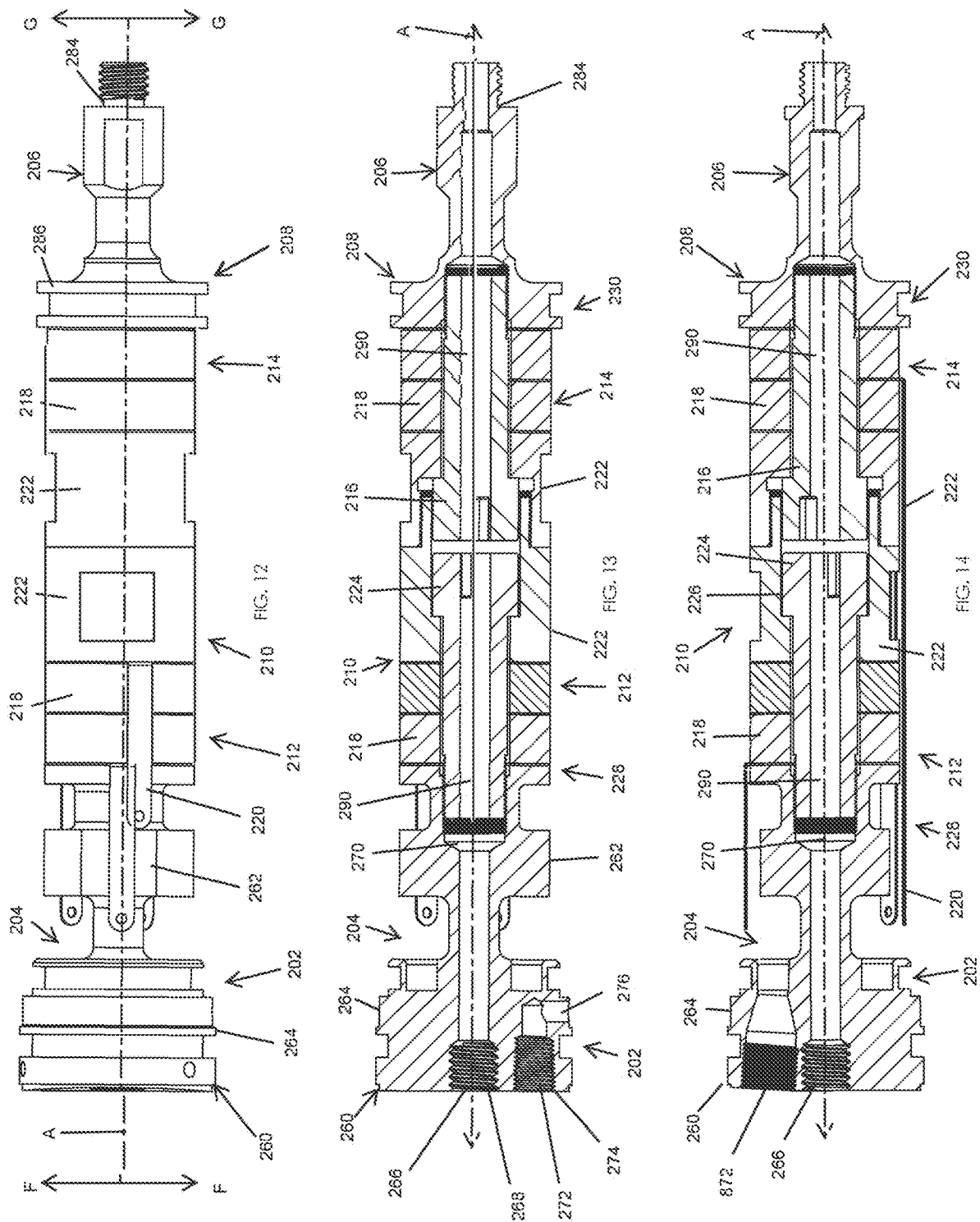

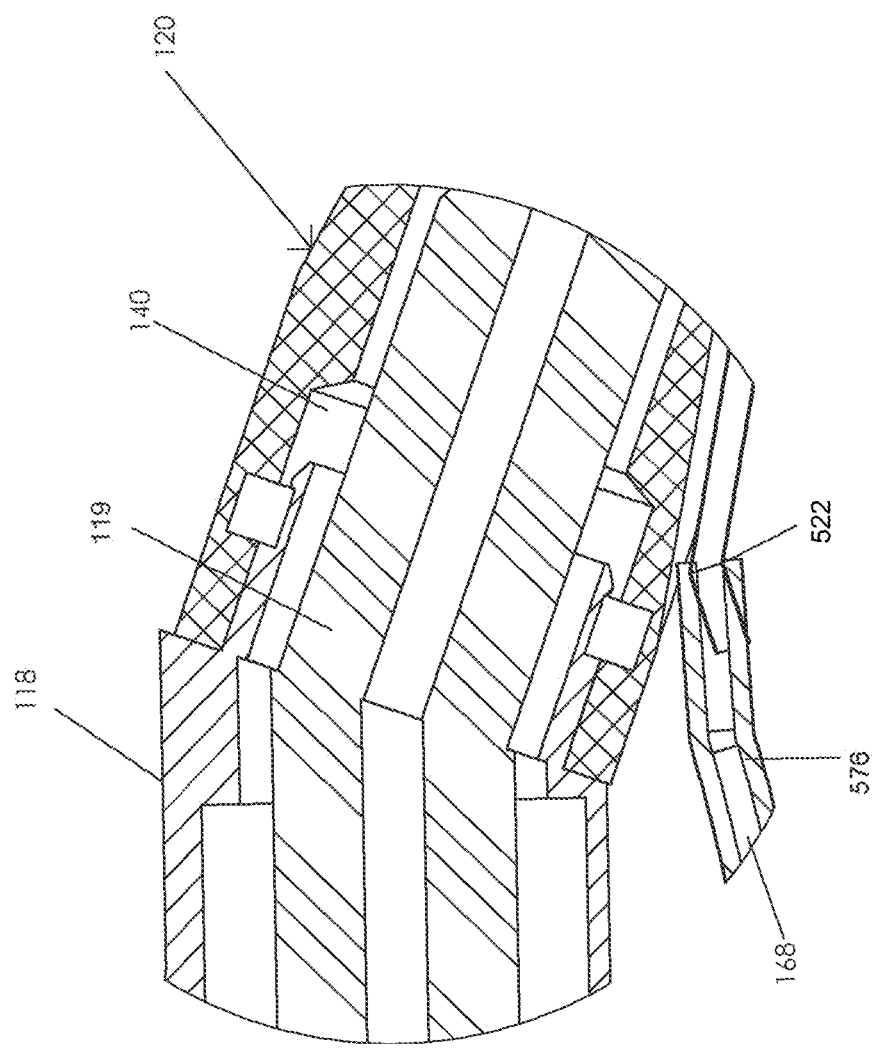

IRRIGATION SYSTEM FOR AN ULTRASONIC SURGICAL HANDPIECE

CROSS-REFERENCE TO RELATED APPLICATIONS

This non-provisional application claims priority to U.S. Provisional Application Ser. No. 62/741,606 filed Oct. 5, 2018, the entire disclosure of which is incorporated herein by reference.

STATEMENT REGARDING FEDERALLY SPONSORED RESEARCH

Not applicable.

BACKGROUND

The present invention relates to an irrigation system for an ultrasonic surgical device, and more particularly, the present invention relates to an irrigation system having a separated irrigation path to prevent irrigation fluid from contacting an operational portion of a surgical attachment of the ultrasonic surgical device to reduce power loss along the surgical attachment.

Ultrasonic surgical devices are used in surgical procedures for various applications, such as, dissection, aspiration, coagulation, and cutting of biological tissue. Typically, ultrasonic surgical devices use piezoelectric transducers to operate by generating a high frequency wave oscillation that vibrates various surgical tools at a resonant frequency. Compared to traditional surgical tools and techniques, ultrasonic surgical devices provide numerous advantages. For example, ultrasonic vibration provides more precise cutting and better coagulation of the tissue than electro-surgical instruments, thereby reducing bleeding and reduced damage to surrounding tissue. In addition, ultrasonic vibration provides for less thermal damage, such as charring, and less desiccation than cryogenic or electro-surgical instruments.

Generally, ultrasonic surgical devices are handheld devices that are manually controlled by surgeons during the surgical procedure. Hence, ultrasonic surgical devices typically have design constraints on their size and geometry to accommodate their handheld nature. In turn, such constraints affect the size and capabilities of operational components within the surgical device. For example, design constraints on size and geometry limit the size, geometry, and power of motors and surgical attachments. Therefore, power efficiency in such surgical devices can be critical. Any loss or reduction of power can reduce the effectiveness and capabilities of the surgical device.

In surgical procedures, irrigation fluid is often provided at the surgical site for various benefits, such as to cool the tissue and the tip of the surgical device. In some applications, a separate irrigation hose is used and held at the surgical site to provide irrigation fluid. In other applications, the surgical device may include an integrated irrigation system within the surgical device. For example, the surgical device may include an external irrigation tube attached along the outer surface of the surgical device to communicate irrigation fluid from an irrigation fluid source to the surgical site. Alternatively, the surgical device may include an internal irrigation tube or irrigation channel.

Typically, internal irrigation paths communicate irrigation fluid along the length of the handpiece to provide cooling to the components, such as the motor and the surgical attachment. For example, the irrigation fluid can flow through the handpiece and come into direct contact with the components. However, contact between the irrigation fluid and the surgical attachment can cause a dampening effect that reduces the power along the length of the surgical attachment, thereby limiting the effectiveness and capabilities of the handpiece to operate at the surgical site.

Therefore, there is a need for an ultrasonic surgical handpiece using a separated internal irrigation path to prevent irrigation fluid contacting an operational portion of a surgical attachment of an ultrasonic surgical device to reduce power loss.

BRIEF DESCRIPTION

In one embodiment, an ultrasonic surgical handpiece includes a motor having a transducer assembly along a central axis of the surgical handpiece. The motor is configured for operative connection to a power source. A surgical attachment has a proximal end detachably connected to the motor and a distal end defining a working plane for engagement with biological tissue. A housing has a housing distal end, a housing proximal end, and a cavity configured to receive the motor and the surgical attachment. An irrigation path of the housing is configured to communicate irrigation fluid. The irrigation path has an inlet proximate the housing proximal end operatively connected to an irrigation fluid source, and an outlet proximate to the working plane. The irrigation path is separated from the housing cavity to prevent contact between the irrigation fluid and an operational portion of the surgical attachment.

In another embodiment, an ultrasonic handpiece includes a motor having a transducer assembly along a central axis of the surgical handpiece. The motor is configured for operative connection to a power source. A surgical attachment has a proximal end detachably connected to the motor and a distal end defining a working plane for engagement with biological tissue. The ultrasonic handpiece includes an irrigation assembly having a housing with a housing distal end, a housing proximal end, and a cavity configured to receive the motor and the surgical attachment. The irrigation assembly defines an irrigation path configured to communicate irrigation fluid, the irrigation path having an inlet proximate the housing proximal end operatively connected to an irrigation fluid source, and an outlet proximate to the working plane. The irrigation path is separated from the housing cavity to prevent contact between the irrigation fluid and an operational portion of the surgical attachment.

In another embodiment, a method of irrigating a surgical handpiece includes providing a motor having a transducer assembly along a central axis of the surgical handpiece, the motor being configured for operative connection to a power source, providing a surgical attachment having a proximal end detachably connected to the motor and a distal end defining a working plane for engagement with biological tissue, providing a housing having a housing distal end, a housing proximal end, and a cavity configured to receive the motor and the surgical attachment, providing an irrigation path of the housing, the irrigation path having an inlet proximate the housing proximal end operatively connected to an irrigation fluid source, and an outlet proximate to the working plane, wherein the irrigation path is separated from the housing cavity to prevent contact between the irrigation fluid and an operational portion of the surgical attachment, and communicating irrigation fluid through the irrigation path.

BRIEF DESCRIPTION OF THE DRAWINGS

The present inventive subject matter will be better understood from reading the following description of non-limiting embodiments, with reference to the attached drawings, wherein below:

FIG. 12 is a side view of a motor;

FIG. 13 is a cross-section view of the motor taken along section F-F shown in FIG. 12;

FIG. 14 is a cross-section view of the motor taken along section G-G shown in FIG. 12.

FIG. 20 is an enlarged partial cross-section view of the ultrasonic handpiece taken at section D shown in FIG. 17.

Corresponding reference numerals indicate corresponding parts throughout the several figures of the drawings.

DETAILED DESCRIPTION

Figure 1:
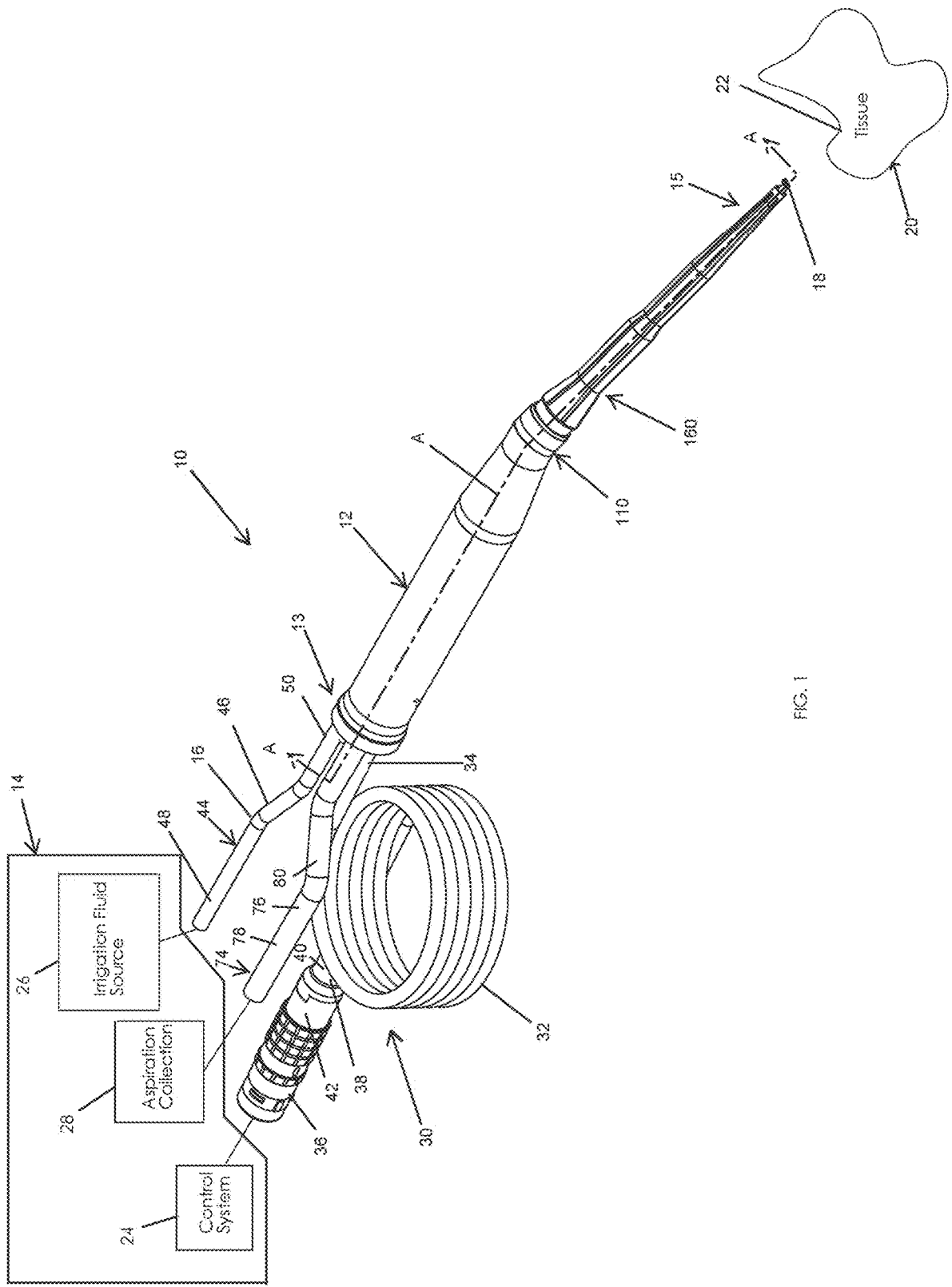
FIG. 1 is a perspective view of an ultrasonic surgical system constructed in accordance with an embodiment.

The following detailed description illustrates the inventive subject matter by way of example and not by way of limitation. The description enables one of ordinary skill in the art to make and use the inventive subject matter, describes several embodiments of the inventive subject matter, as well as adaptations, variations, alternatives, and uses of the inventive subject matter. Additionally, it is to be understood that the inventive subject matter is not limited in its application to the details of construction and the arrangements of components set forth in the following description or illustrated in the drawings. The inventive subject matter is capable of other embodiments and of being practiced or being carried out in various ways. Also, it is to be understood that the phraseology and terminology used herein is for the purpose of description and should not be regarded as limiting on all embodiments of the inventive subject matter.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

Embodiments described herein include ultrasonic surgical systems that have control systems, surgical handpieces, motors, surgical attachments, and irrigation systems used in surgical procedures to engage biological tissue. For example, the ultrasonic surgical system may have a surgical handpiece with a motor, a surgical attachment, and a housing having an irrigation assembly. The irrigation assembly may have a variety of configurations as set forth herein. For example, the irrigation system may be configured to communicate irrigation fluid from an irrigation fluid source to a working plane of the surgical attachment via an irrigation path within the housing that is separated from any contact with an operational portion of the surgical attachment. Optionally, the ultrasonic surgical system may include an aspiration assembly to power and/or aspirate the biological tissue.

FIG. 1 is a perspective view of an ultrasonic surgical system 10 constructed in accordance with an embodiment that includes a surgical handpiece 12 having a distal end 13 operatively connected to a control system 14 with a connection assembly 16. In an exemplary embodiment, the control system 14 is configured to provide power, irrigation fluid, and suction or aspiration at a working plane 18 of a proximal end 15 of the handpiece 12 during a surgical procedure. The working plane 18 of the handpiece 12 may engage biological tissue 20 at a surgical site 22 to perform various surgical procedures, such as, cutting coagulation, irrigation, and aspiration. In alternate embodiments, the handpiece 12 may be configured to engage soft biological tissue, such as, muscular tissue, connective tissue, nervous tissue, epithelial tissue, and the like, or hard biological tissue, such as, bone, enamel, dentin, cementum, and the like. The surgical handpiece 12 includes an irrigation assembly 110 configured to communicate irrigation fluid from the control system 14 to the working plane 18 of the handpiece 12 through an irrigation path 160.

Figure 2:
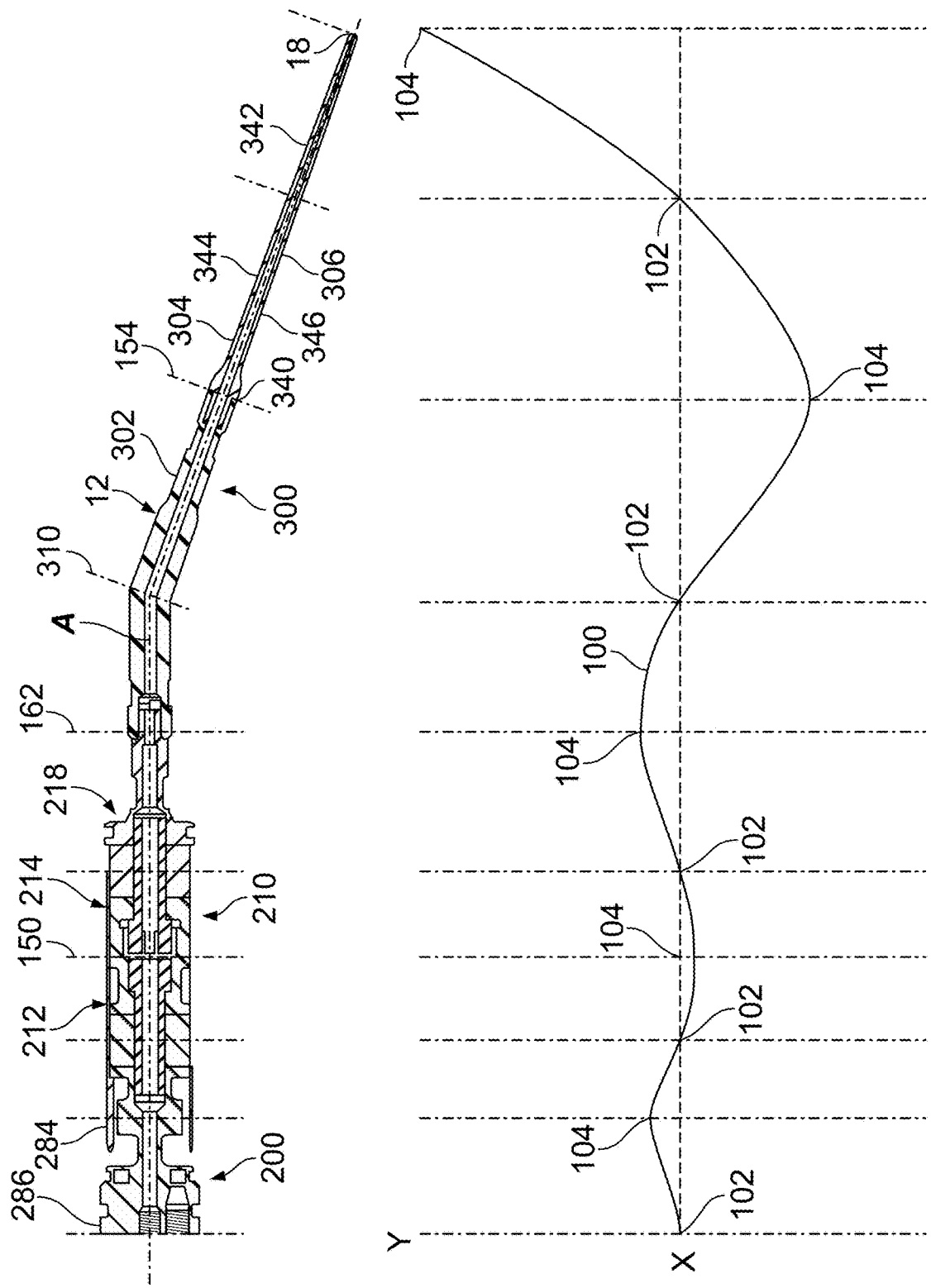
FIG. 2 is a cross-section view of the ultrasonic surgical handpiece with a housing removed taken along section A-A shown in FIG. 1 and a corresponding schematic illustrating a standing wave along the ultrasonic surgical handpiece in accordance with an embodiment.

FIG. 2 is a cross-section view of the ultrasonic surgical handpiece 12 with a housing 111 removed taken along section A-A shown in FIG. 1 and a corresponding schematic illustrating the standing wave 100 along the ultrasonic surgical handpiece 12 in accordance with an embodiment. In response to the application of electrical current and voltage from the control system 14, the handpiece 12 creates a standing wave 100 along the central axis A with an alternating pattern of nodes 102 and anti-nodes 104 located at various positions along the central axis A. The X-axis of the schematic illustrates the position of the nodes 102 and anti-nodes along the central axis A of the handpiece 12. The Y-axis illustrates the amplitude of the standing wave 100 along the central axis A of the handpiece 12.

For example, anti-nodes 104 are located at a proximal end 284 of a connector block 202, at an interface 150 between a first stack 212 and a second stack 214 of a transducer assembly 210, an interface 152 between an amplifier 206 and a surgical attachment 300, an interface 154 between an angled adapter 302 and an ultrasonic tip 304, and at the working plane 18. For example, the distance between anti-nodes 104 along the handpiece 12 are (from distal end to the proximal end) about 0.903" inches, about 0.5922" inches, about 0.658" inches, about 1.087" inches, about 1.057" inches, about 1.66" inches, about 1.626" inches, and about 1.365" inches. For example, the amplitude of the standing wave 100 progressively increases along the central axis A of the handpiece 12 approaching the proximal end 15 of the handpiece 12, with the maximum amplitude being at the working plane 18.

Generally, the standing wave 100 may be described as a wave that oscillates in time but whose peak amplitude profile does not move in space. The standing wave 100 may represent the distribution of motion along the length of the surgical handpiece 12 whose amplitude varies harmonically in time but remains spatially stationary. The peak amplitude of the wave oscillations at any point in space is constant in time, and the oscillations at different points throughout the wave are in phase with each other. The standing wave pattern defines an alternating pattern of nodal positions, such as nodes and anti-nodes. When a standing wave is established, the nodes and anti-nodes remain located at the same position along the medium. A node of the standing wave is a location at which the amplitude of the standing wave is minimum, which may include zero. At the nodes, there is minimal to no displacement during each vibrational cycle. The standing wave 100 may be formed by the interference of two traveling waves. Therefore, nodes are produced at locations where destructive interference occurs. An anti-node of the standing wave is a location at which the amplitude of the standing wave is maximum. At the anti-nodes, there is a maximum displacement during each vibrational cycle. The anti-node vibrates back and forth between a positive displacement and a negative displacement. Anti-nodes are produced at locations where constructive interference occurs.

Figure 3:
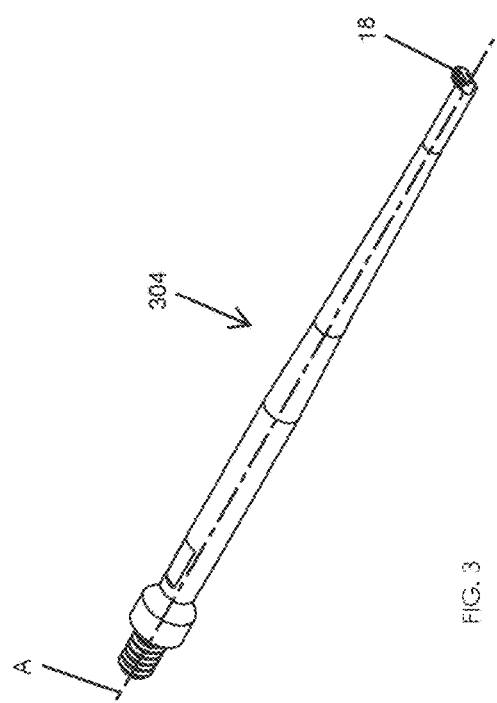
FIG. 3 is a perspective view of an ultrasonic tip in accordance with an embodiment.
Figure 4:
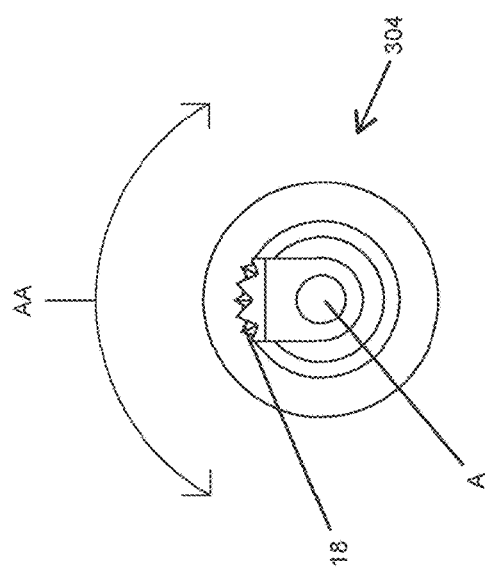
FIG. 4 is an end view of the ultrasonic tip illustrating torsional motion at a working plane in accordance with an embodiment.

FIG. 3 is a perspective view of an ultrasonic tip 304 in accordance with an embodiment. FIG. 4 is an end view of the ultrasonic tip 304 illustrating torsional motion at the working plane 18 in accordance with an embodiment. The standing wave 100 created along the handpiece 12 results in torsional motion about the central axis A at the working plane 18 of the surgical attachment 300. For example, the amplitude AA of the tip 304 at the working plane 18 may be a maximum of about 18 mils peak-to-peak (450 microns) with an operating resonance frequency of in a range of about 24500 to about 25500 Hz. However, alternate embodiments may produce other amplitudes at the working plane 18 and/or with other operating resonance frequencies. In addition, alternate embodiments may produce longitudinal, longitudinal-torsional, or other motion at the working plane 18.

Referring again to FIG. 1, the control system 14 includes a power source 24 that provides electrical current and power to the handpiece 12 via the connection assembly 16. For example, the handpiece 12 may have an operating frequency in a range of 24500 to 25500 Hz and be driven by the control system 14 with power in a range of 85 to 110 watts. In alternate embodiments, the handpiece 12 may have an operating frequency of less than 24500 Hz or greater than 25500 Hz and be driven with power of less than 85 watts or greater than 110 watts.

Figure 6:
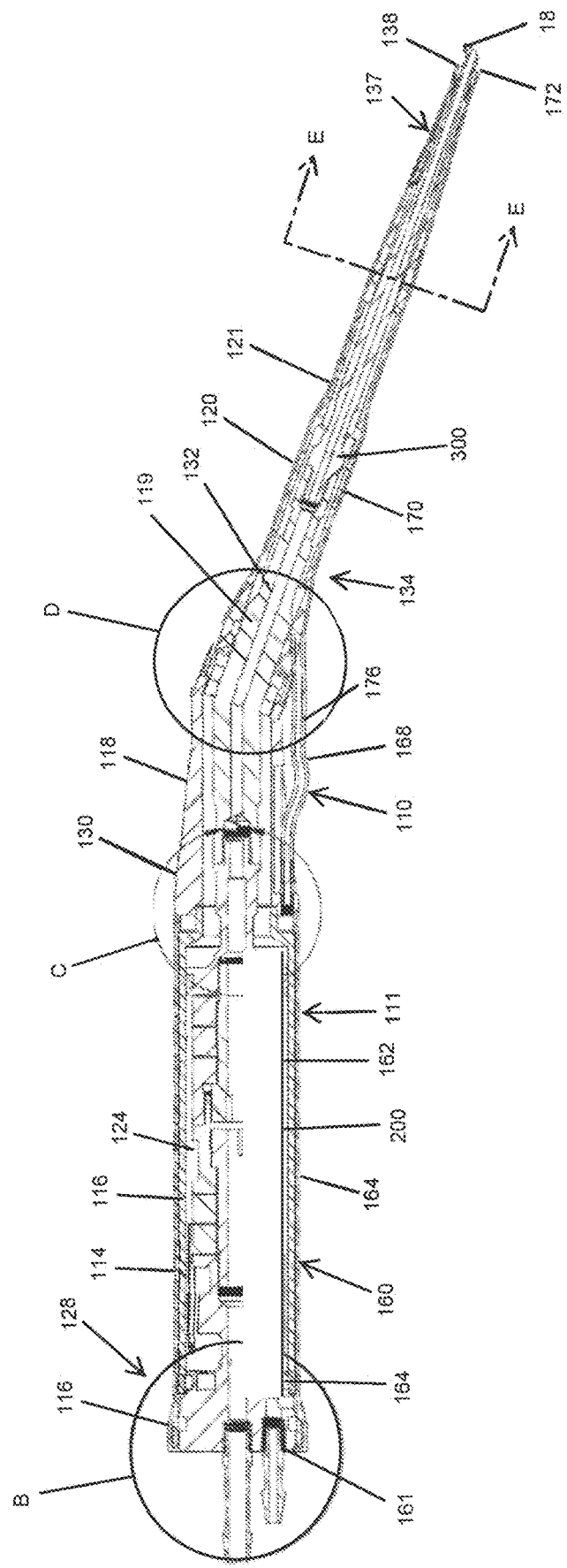
FIG. 6 is a cross-section view of the ultrasonic surgical handpiece taken along section A-A shown in FIG. 1.

An exemplary embodiment of the control system 14 also includes an irrigation fluid source 26 configured to provide irrigation fluid to the irrigation assembly 110 of the handpiece 12 via the connection assembly 16. In one embodiment, the irrigation assembly 110 may be configured to communicate irrigation fluid through one or more irrigation paths 160 of the handpiece 12 to the working plane 18 and the surgical site 22 for use as a cooling medium and irrigation (FIG. 6). For example, the irrigation fluid source 26 may include an irrigation pump (not shown), such as a peristaltic pump, configured to pump water from a water source to the irrigation assembly 110 via the connection assembly 16.

In addition, an exemplary embodiment of the control system 14 includes an aspiration collector 28 to provide suction to the handpiece 12 via the connection assembly 16. In one embodiment, the handpiece 12 may be configured to provide suction through a suction channel of the handpiece 12 to the working plane 18 and the surgical site 22 for use as aspiration. For example, the aspiration collector 28 may include a vacuum pump (not shown), configured to create a vacuum to the handpiece 12 via the connection assembly 16 to communicate aspirated biological tissue from the working plane 18 and surgical site 22 to a biological waste cannister (not shown).

In the illustrated embodiment, the connection assembly 16 includes an electrical connection 30 that transmits electrical power from the power source 24 of the control system 14 to the handpiece 12. For example, the electrical connection 30 includes an electrical cable 32 having a proximal end 34 coupled with the handpiece 12, and an electrical connector 36 attached to a distal end 38 of the cable 32. Optionally, a strain relief 40 is attached at a cable end 42 of the electrical connector 36. As illustrated, the electrical connector 36 is a high-voltage modular connector, such as, a connector manufactured by LEMO®, that detachably connects with the control system 14. However, in alternate embodiments, the connector may be any suitable connector capable of operatively connecting with the control system 14.

The connection assembly 16 also includes an irrigation connection 44 that transmits irrigation fluid from the irrigation fluid source 26 of the control system 14 to the irrigation assembly 110 of the handpiece 12. For example, the irrigation connection includes a tube 46 having a distal end 48 connected to the control system 14 and a proximal end 50 coupled with the handpiece 12, such as with an irrigation barb 52 (FIG. 5).

The connection assembly 16 also includes an aspiration connection 74 that transmits aspirated material from the handpiece 12 to the aspirator collector 28 of the control system 14. For example, the aspirator connection 74 includes a tube 76 having a distal end 78 connected to the control system 14 and a proximal end 80 coupled with the handpiece 12, such as with an aspiration barb 82 (FIG. 5).

In one or more embodiments, the irrigation barb 52 and/or the aspiration barb 82 may be manufactured from any suitable material, including, but not limited to, polymers, metals, metal alloys, any combination thereof. For example, irrigation barb 52 and/or the aspiration barb 82 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, irrigation barb 52 and/or the aspiration barb 82 may be manufactured from an underdamped material, a material having a Q factor greater than 0.5, a metal alloy in an annealed condition, a titanium alloy in an annealed condition, or from Ti-6Al-4V extra-low interstitials in an annealed condition.

Figure 5:
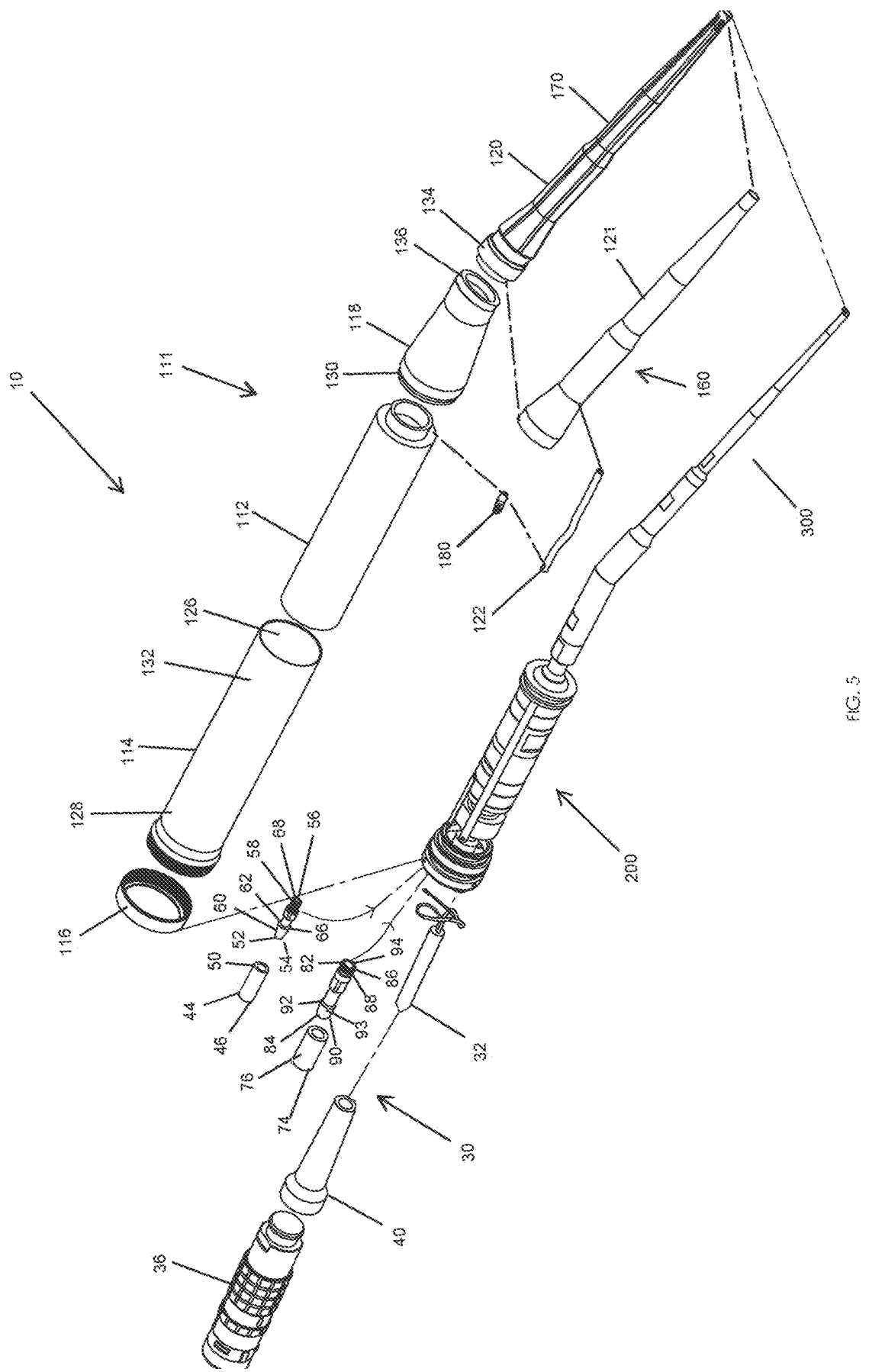
FIG. 5 is a partially exploded perspective view of an ultrasonic surgical handpiece with a housing removed and a connection assembly in accordance with an embodiment.

FIG. 5 is a partially exploded perspective view of the ultrasonic surgical handpiece 12 with the housing 111 removed and a connection assembly 16 in accordance with an embodiment that includes a motor 200 and a surgical attachment 300. FIG. 6 is a cross-section view of the ultrasonic surgical handpiece 12 taken along section A-A shown in FIG. 1. In an exemplary embodiment, the irrigation assembly 110 includes the housing 111 having an inner housing member 112, an outer housing member 114, a collar 116, a nose cone 118, an irrigation member 120, an irrigation member sleeve 121, and an bypass tube 176 that detachably assemble to receive the motor 200 and the surgical attachment 300 and define an irrigation path 160 that communicates irrigation fluid from the irrigation connection 44 to the working plane 18. The irrigation path 160 includes an inlet 161, an inlet channel 164, an intermediate channel 162, a bypass channel 168, an outlet channel 170, and an outlet 172.

Figure 7:
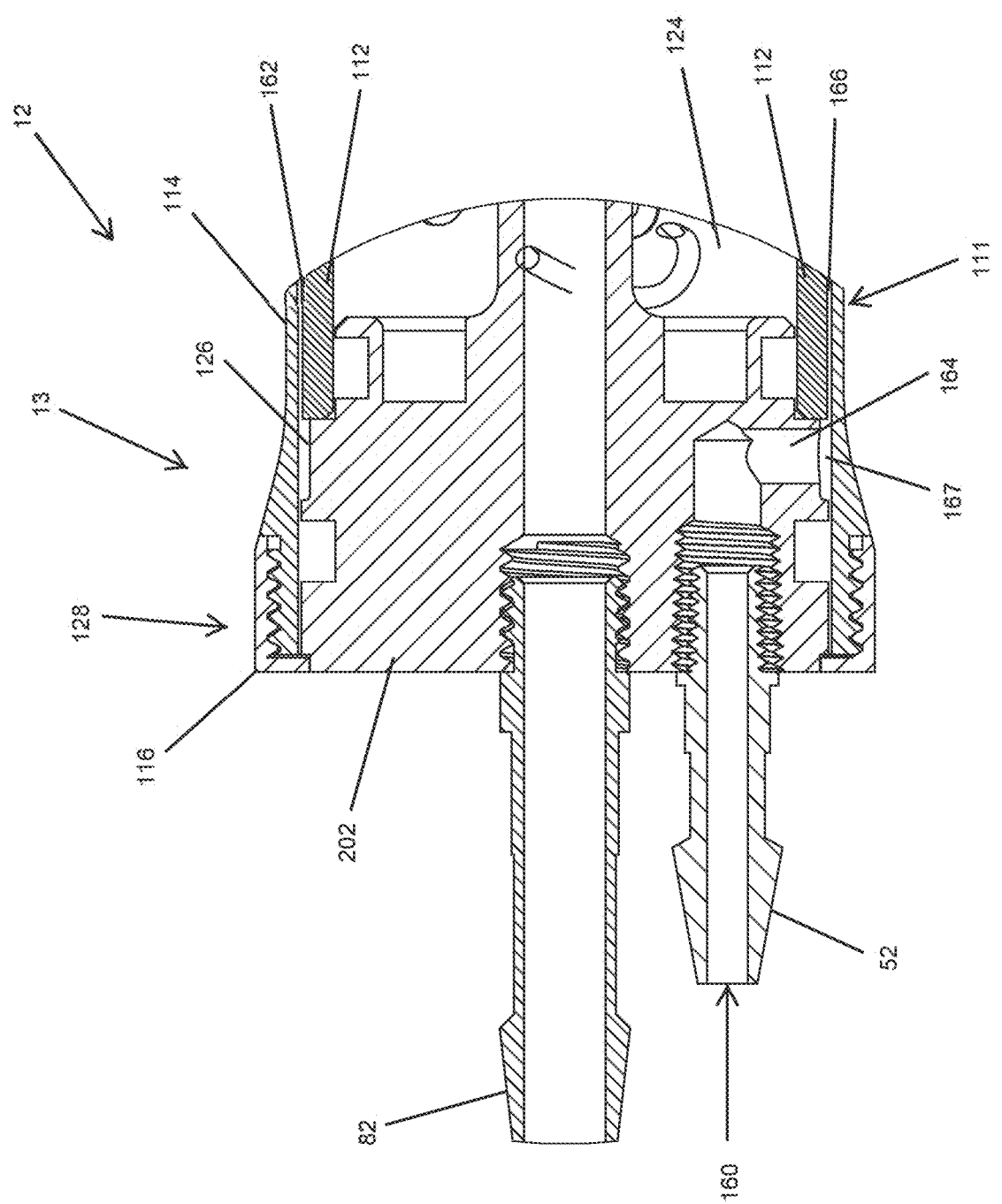
FIG. 7 is an enlarged partial cross-section view of the ultrasonic handpiece taken at section B shown in FIG. 6.

FIG. 7 is an enlarged partial cross-section view of the ultrasonic handpiece 12 taken at section B shown in FIG. 6. In an exemplary embodiment, the irrigation path 160 includes the inlet channel 164 at the distal end 13 of the handpiece 12 configured to operatively connect the irrigation connection 44 to the intermediate channel 162 of the housing 111. For example, the inlet channel 164 may extend through the irrigation barb 52 and a connector block 202.

In an exemplary embodiment, the intermediate channel 162 extends through the length of the housing 111 to operatively connect to the bypass channel 168 (FIG. 6). For example, the generally cylindrical inner housing member 112 includes a cavity or bore 124 configured to receive the motor 200 (FIG. 5). The generally cylindrical outer housing member 114 includes a bore 126 configured to receive the inner housing member 112 and motor 200 and defines the generally annular intermediate channel 162 between an outer surface of the inner housing member 112 and an inner surface of the outer housing member 114. The intermediate channel 162 may define annular grooves 167 at each end. In operation, the irrigation fluid flows through the intermediate channel 162 without any physical contact with the motor 200. However, the irrigation fluid may provide cooling to the motor 200 as it flows through the intermediate channel 162 by receiving heat from the motor 200 by thermal conduction and/or convention through the inner housing member 112. The collar 116 detachably couples with a distal end 128 of the outer housing member 114, such as with a threaded connection. The nosecone 118 includes a distal end 130 configured to detachably couple, such as with a threaded connection, with a proximal end 132 of the outer hosing member 126. The nosecone 118 includes a bore 119 configured to receive at least a portion of the surgical attachment 300, such as an angled adaptor 302.

Figure 8:
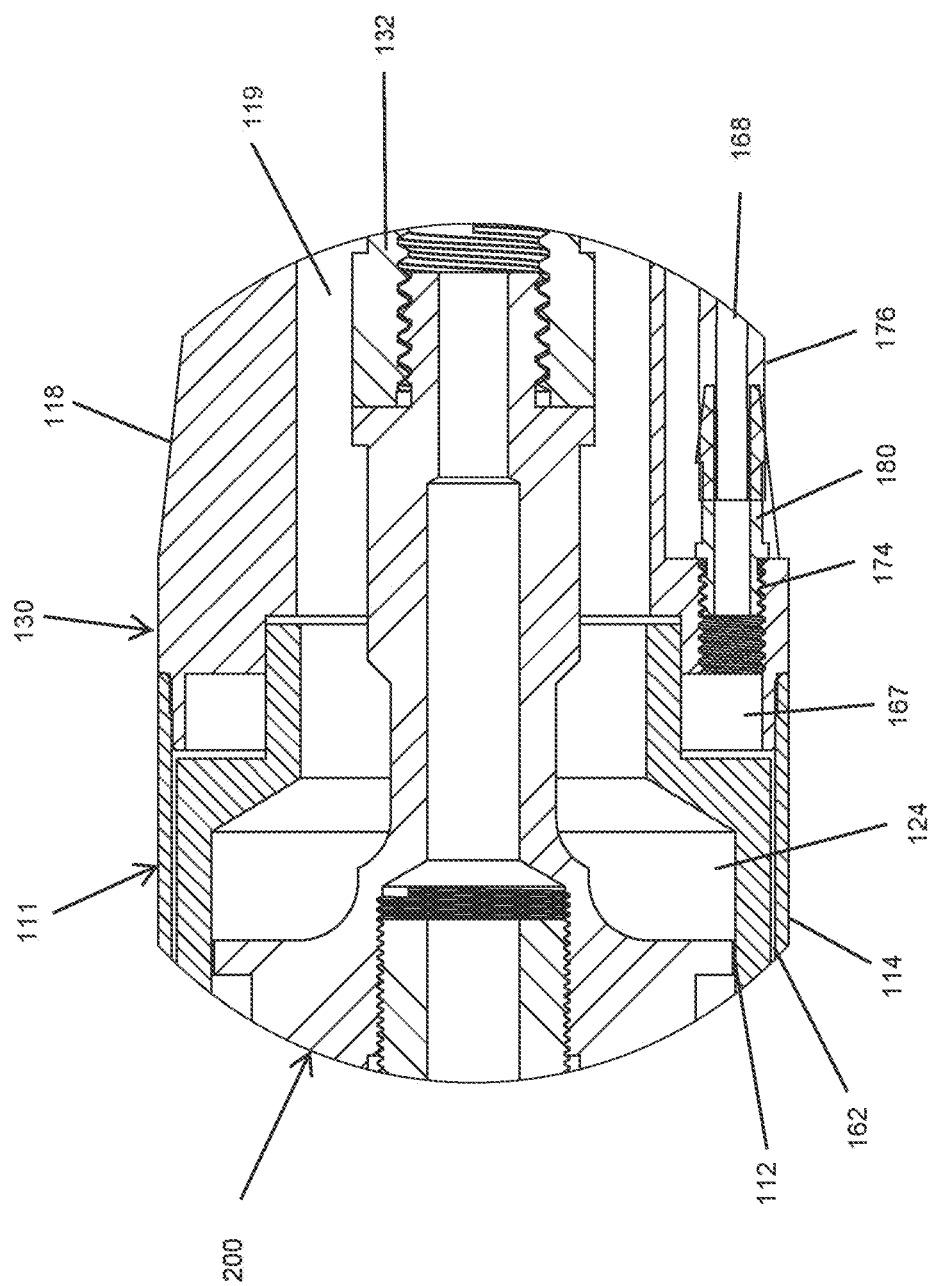
FIG. 8 is an enlarged partial cross-section view of the ultrasonic handpiece taken at section C shown in FIG. 6.
Figure 9:
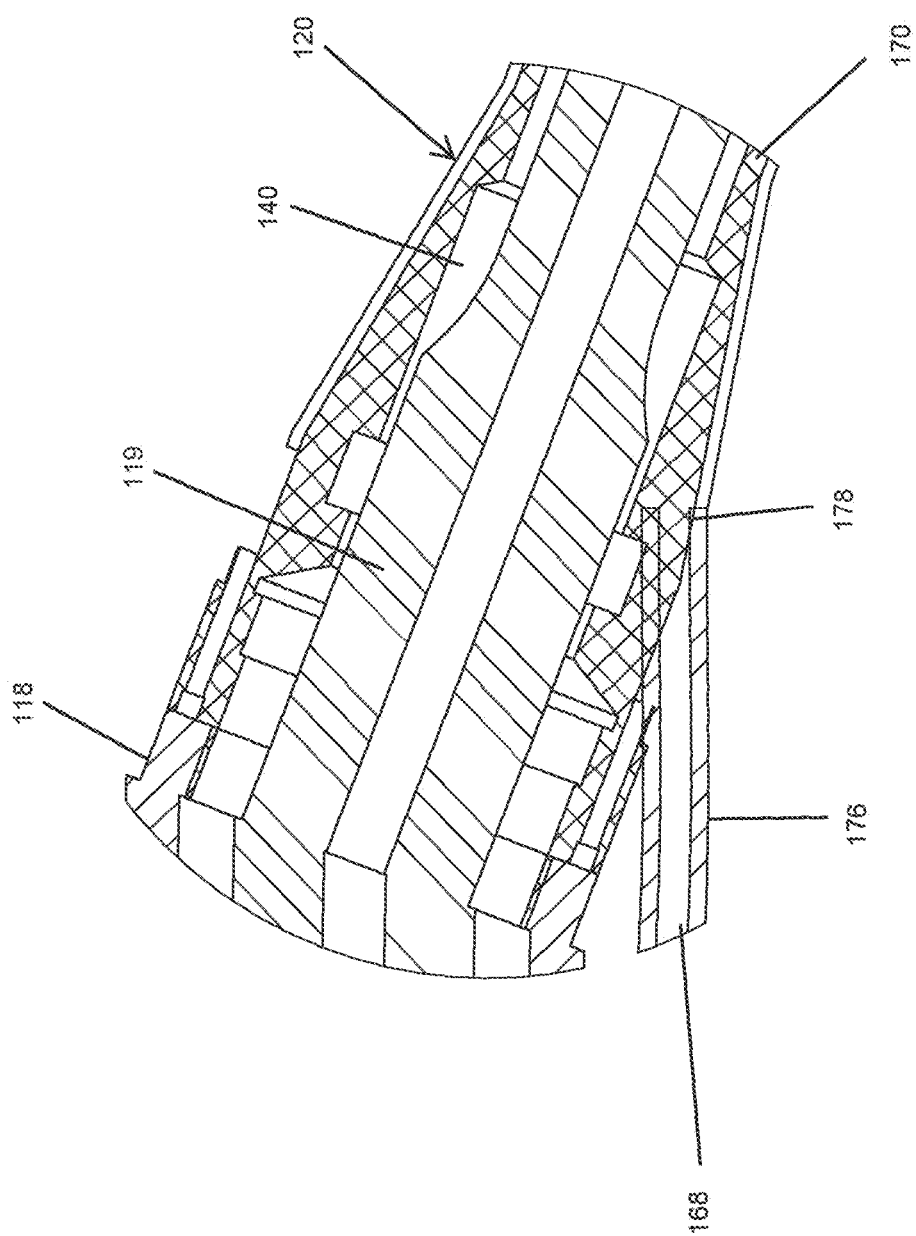
FIG. 9 is an enlarged partial cross-section view of the ultrasonic handpiece taken at section D shown in FIG. 6.

FIG. 8 is an enlarged partial cross-section view of the ultrasonic handpiece 12 taken at section C shown in FIG. 6. FIG. 9 is an enlarged partial cross-section view of the ultrasonic handpiece 12 taken at section D shown in FIG. 6. In an exemplary embodiment, the bypass channel 168 is configured to operatively connect the intermediate channel 162 with the outlet channel 170. For example, the nosecone 118 may include a bypass outlet 174 with a bypass tube 176 extending from the bypass outlet 174 a bypass inlet 178 of the irrigation member sleeve 121. The bypass tube 176 may engage with the bypass inlet 178 and/or bypass outlet 174 in any suitable manner. For example, the bypass tube 176 may detachably connect to the bypass inlet 178 and/or bypass outlet 174 using a connector 180, such as a barb. Alternatively, the bypass tube 176 may attach to the bypass inlet 178 and/or bypass outlet 174 using an adhesive, welding, fastener, or the like. In the exemplary embodiment, the bypass tube 176 comprises a flexible material, such as a polymer. However, any suitable material can be used, including, but not limited to metals, metal alloys, etc., or from any combination of suitable materials.

Figure 10:
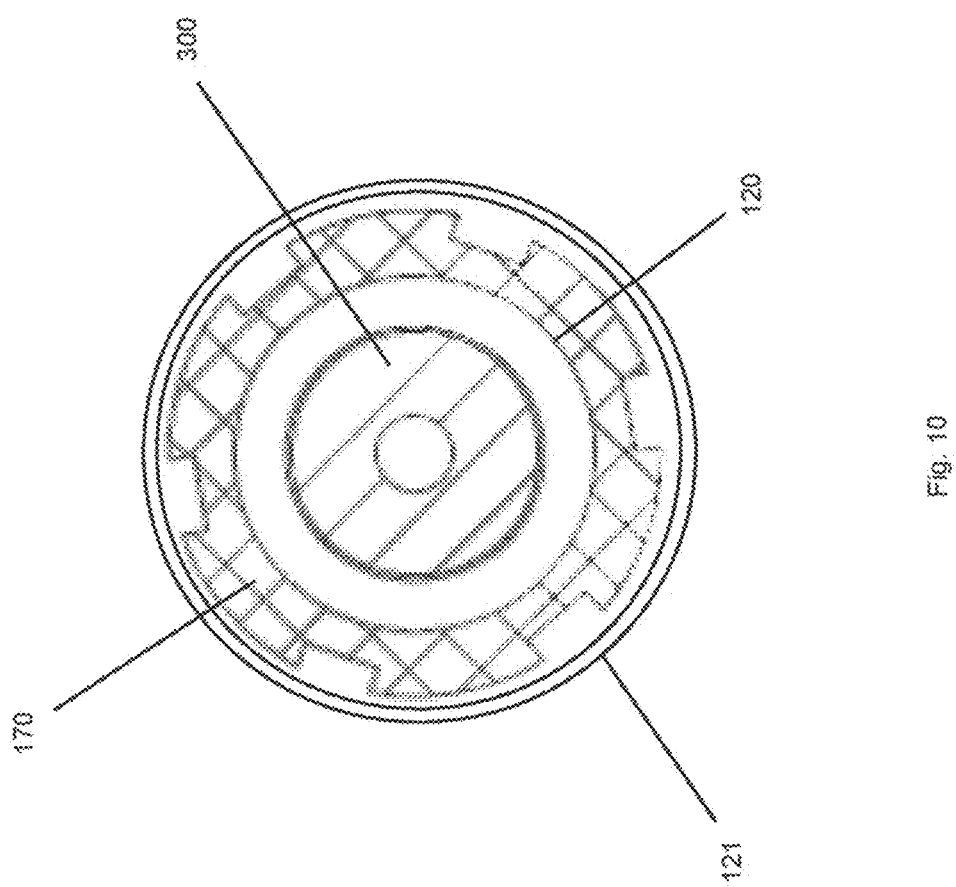
FIG. 10 is an enlarged partial cross-section view of the ultrasonic handpiece taken along section E-E shown in FIG. 6.

FIG. 10 is an enlarged partial cross-section view of the ultrasonic handpiece 12 taken along section E-E shown in FIG. 6. The irrigation member 120 includes a distal end 134 configured to detachably couple, such as with a threaded connection, with a proximal end 136 of the nosecone 118 and includes a bore 140 configured to receive a portion of the surgical attachment 300 (FIG. 6). The irrigation member 120 includes one or more outlet channels 170 configured to operatively connect the intermediate channel 162 to the outlet 172. For example, an outer surface 142 of the of the irrigation member 120 defines a plurality of generally longitudinal grooves, that extend from the distal end 134 of the irrigation member 120 to the outlet 138 at a proximal end 137 of the irrigation member 120 (FIG. 6). The irrigation member sleeve 121 surrounds the outer surface 142 of the irrigation member 120 and covers the longitudinal grooves to form one or more outlet channels 170 (FIG. 10). The outlet 138 is configured to direct irrigation fluid to the working plane 18 and surgical site 22. The irrigation member sleeve 121 may be comprised of any suitable material, including but limited to a heat-shrink material, a tape material, a liquid polymer dip material, and the like.

In operation, the irrigation fluid flows through the irrigation path 160 without contact with an operational portion 190 of the surgical attachment 300. In the exemplary embodiment, the operational portion of the surgical attachment 300 includes the portion disposed between the distal end 308 of the surgical attachment 300 to an interface 192 proximate with the outlet 138. In this way, the irrigation fluid is separated from contact with the operational portion 190 of the surgical attachment so as not to dampen the motion.

In one or more embodiments, each component of the housing 111 may be manufactured from any suitable material, including, but not limited to, polymers, metals, metal alloys, any combination thereof.

Figure 11:
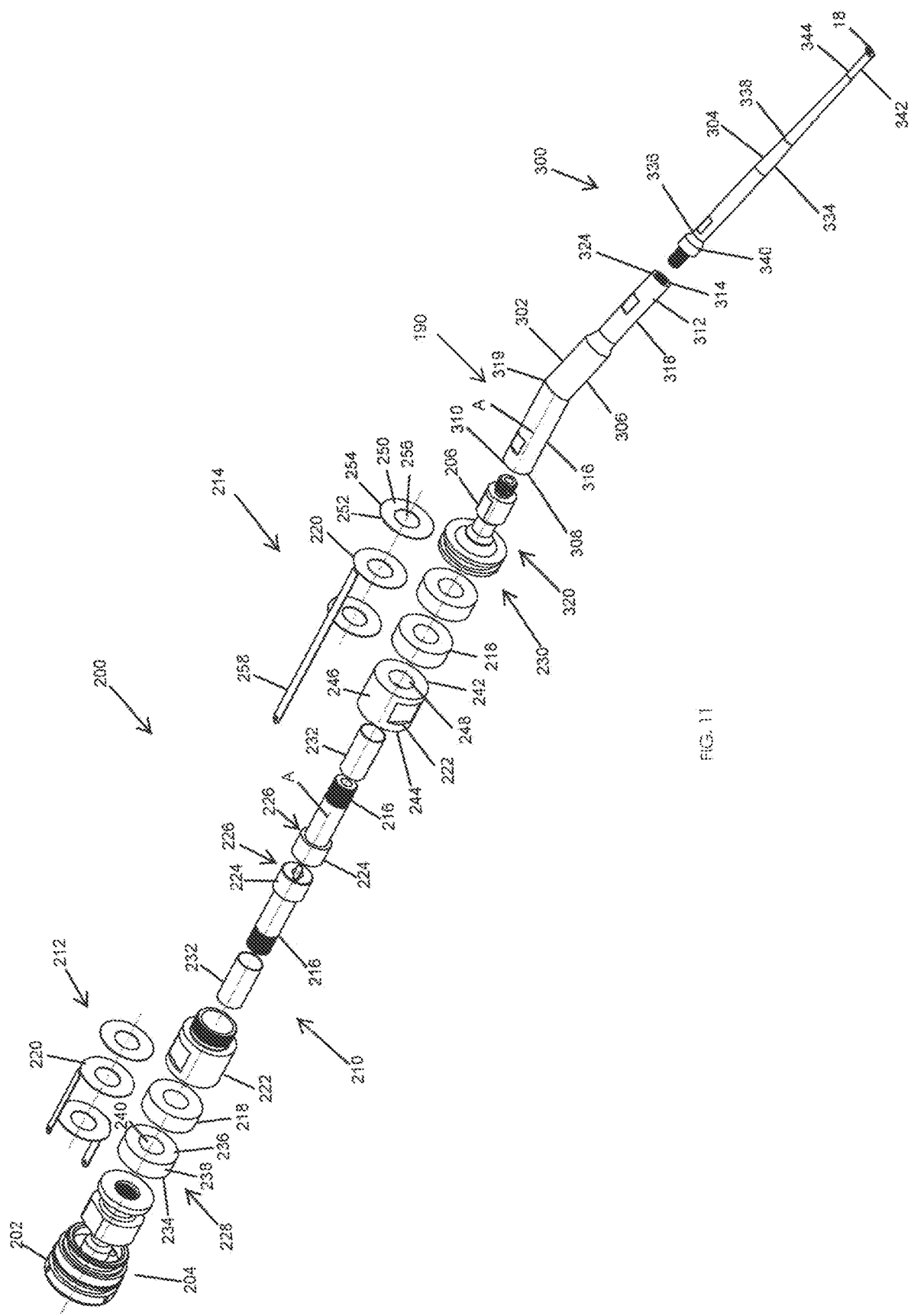
FIG. 11 is an exploded perspective view of a motor and surgical attachment of the ultrasonic surgical handpiece in accordance with an embodiment.

FIG. 11 is an exploded perspective view of a motor 200 and surgical attachment 300 of the ultrasonic surgical handpiece 12 in accordance with an embodiment. In an exemplary embodiment, the surgical attachment 300 includes an angled adaptor 302 and an ultrasonic tool or tip 304 aligned along the central axis A of the handpiece 12. The angled adaptor 302 includes a body 306 having a distal end 308 detachably connected to the motor 200, such as with a threaded bore 310, and a proximal end 312 detachably connected to the tip 304, such as with a threaded bore 314. The body 306 includes a distal portion 316 and a proximal portion 318 offset from each other at angle at a junction 319, such as an angle in the range of about 10°-45°, however, any angle can be used. The angled adaptor 302 may comprise an amplifier interface 320 at the distal end 308, and angled tip interface 324 at the proximal end 312. In one or more embodiments, angled adaptor 302 may comprise angled adaptor bore 330 and a tip bore 332 (FIG. 6). As shown in FIG. 2, the junction 319 is positioned to correlate with a node of the standing wave 100. The correlation of the junction 319 with node 102 increases the amplitude of the standing wave 100 after the junction 319 as it approaches the working plane 18.

In an exemplary embodiment, an ultrasonic tip 304 includes a body 334 having a distal end 336 detachably connected to the proximal end 312 of the angled adaptor 302, such as with a threaded portion, and a proximal end 338 having a working plane 18 configured for engagement of biological tissue. The body 334 may include a plurality of portions having discretely different dimensions to correspond to the nodes 102 and anti-nodes 104 of the standing wave. For example, the body 306 may include a base portion 340 at the distal end 336, a tip portion 342 at the proximal end 338, and a sloped intermediate portion 344 disposed between the base portion 340 and the tip portion 342. A bore 346 extends through the length of body 334 along the center axis A. The ultrasonic tip 304 is configured so that when the handpiece 12 is assembled, the position of the working plane 18 corresponds to one of the anti-nodes 104 of the standing wave 100.

In alternate embodiments of the surgical attachment 300, the angled adaptor 302 and ultrasonic tip 304 may be configured using dimensions that correspond to position of the working plane 18 with an anti-node 104 of the standing wave 100. For example, the ultrasonic tip 304 may have an overall length between distal end 316 and proximal end 318 in a range of about 2.9" inches to about 3.1" inches. The base portion 340 may have a diameter in a range of about 0.2" inches to about 0.3" inches. In alternate embodiments of the surgical attachment 300, the ultrasonic tip 304 may be configured to accomplish various surgical procedures. For example, the ultrasonic tip 304 and in particular the tip portion 342 at the working plane 18 may be configured to engage soft biological tissue, such as, muscular tissue, connective tissue, nervous tissue, epithelial tissue, and the like, or hard biological tissue, such as, bone, enamel, dentin, cementum, and the like.

In one or more embodiments, the angled adaptor 302 and/or the tip 304 may be manufactured from any suitable material, including, but not limited to, polymers, metals, metal alloys, any combination thereof. For example, angled adaptor 302 and/or the tip 304 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, angled adaptor 302 and/or the tip 304 may be manufactured from an underdamped material, a material having a Q factor greater than 0.5, a metal alloy in an annealed condition, a titanium alloy in an annealed condition, or from Ti-6Al-4V extra-low interstitials in an annealed condition.

FIG. 12 is a side view of the motor 200. FIG. 13 is a cross-section view of the motor 200 taken along section F-F shown in FIG. 12. FIG. 10 is a cross-section view of the motor 200 taken along section G-G shown in FIG. 12. In an exemplary embodiment, the motor 200 includes a connector block 202 at a distal end 204, an amplifier 206 at a proximal end 208, and a transducer assembly 210 disposed between the connector block 202 and the amplifier 206. The connector block 202, transducer assembly 210, and amplifier 206 are aligned along a central axis A of the handpiece 12 and configured for operative connection to the power source 24 via the connection assembly 16 (FIG. 1).

The transducer assembly 210 includes the first stack 212 and the second stack 214 aligned along the center axis A in opposition to each other about interface 150 (FIG. 6). In the exemplary embodiment, the interface 150 of the first stack 212 and second stack 214 correlates with the position of an anti-node 104 (FIG. 2). The position of the stacks 212, 214 relative to the nodes 102 and anti-nodes 104 place the stacks 212, 214 within zones of minimal amplitude to reduce mechanical stress and power loss on the transducer assembly 210.

The stacks 212, 214 are configured to operate or resonate as a full-wavelength resonator. Each stack 212, 214, includes a shaft or bolt 216 configured to couple with a plurality of torsional transducers 218, a set of electrodes 220, and an inert ring 222 (FIG. 6). For example, the shaft 216 may include a raised collar 224 at a proximal end 226 to abut with the inert ring 222 with a pair of torsional transducers 218 adjacent the inert ring 222. A distal end 228 of the first stack 212 is connected to the connector block 202, and a distal end 230 of the second stack 214 is connected to amplifier 206. A set of three electrodes 220 are disposed between the components and operatively connected to the control system 14 via the electrical connection 30 of the connection assembly 16 (FIG. 1). An insulator 232 is disposed between the shaft 216, the torsional transducers 218, the electrodes 220, and the inert ring 222 to provide electrical insulation between the components. For example, the insulator 232 may be a generally cylindrical sleeve comprised of any suitable electrically insulating material, such as a thermoplastic polymer material. When assembled, the transducer assembly is placed under a predetermined amount of pre-stress to provide for proper interfacing between components. For example, the transducer assembly 210 is placed under pre-stress. In alternate embodiments, the transducer assembly 210 may include any number of stacks of torsional transducers, including a single stack.

In the illustrated embodiment, each torsional transducer 218 is a piezoelectric ring configured to convert electrical energy into ultrasonic vibrations. Each transducer 218 includes a distal end surface 234, and proximal end surface 236, a generally annular outer surface 238, and a bore 240. The end surfaces 234, 236 may be generally smooth to increase the acoustic contact between transducers 218 when assembled. For example, the end surfaces 234, 236 may be absent of any coatings and polished to a surface roughness in a range of about 2 Ra to 6 Ra. In alternate embodiments, each ring may include a coating (not shown) on one or more of the surfaces with a predetermined thickness. The coating may be manufactured from an electrically conductive material, such as, aluminum, an aluminum alloy, silver, a silver alloy, copper, a copper alloy, gold, a gold alloy, platinum, a platinum alloy, tin, a tin alloy, palladium, a palladium alloy, nickel, a nickel alloy, beryllium, a beryllium alloy, tungsten, a tungsten alloy, a steel, chromium, a chromium alloy, titanium, a titanium alloy, and the like.

The dimensions of the transducer 218 are predetermined to achieve the proper piezoelectrical effect. For example, the transducer 218 may have a thickness of about 0.145 to 0.215 inches. However, alternate embodiments may have a thickness of less than 0.145 inches or greater than 0.215 inches. For example, the transducer 218 may have an outer diameter of about 0.465 to 0.655 inches. However, alternate embodiments of may have an outer diameter of less than 0.465 inches or greater than 0.655 inches. For example, the bore 240 of the transducer 218 may have a diameter of about 0.175 to 0.375 inches. However, alternate embodiments may have a diameter of less than 0.175 inches or greater than 0.375 inches.

In an exemplary embodiment, one or more of the torsional transducers 218 may be manufactured from a piezoelectric ceramic material, such as, perovskite material, a lead zirconate titanate ("PZT") material, piezoxide material, a PXE 5 grade material, a PXE 52 grade material, a PXE 59 grade material, a PXE 21 grade material, a PXE 41 grade material, a PXE 42 grade material, a PXE 43 grade material, a PXE 71 grade material, and the like. Alternatively, each transducer may be manufactured from a material having a crystal structure with no center of symmetry, such as, a perovskite crystal structure. In one or more embodiments, each torsional transducer 218 may be manufactured from a material having a tetragonal crystal lattice elementary cell below the material's Curie temperature, such as, a cubic crystal lattice elementary cell above the material's Curie temperature.

In an exemplary embodiment, the inert ring 222 includes a distal end surface 242, and proximal end surface 244, a generally annular outer surface 246, and a bore 248. The dimensions and materials of the transducer 218 are predetermined to achieve the proper configuration of the standing wave 100 along the central axis A, and correspondingly, the position of the nodes 102 and anti-nodes 104. For example, the inert ring 222 may have a thickness of about 0.265 to 0.385 inches. However, alternate embodiments may have a thickness of less than 0.265 inches or greater than 0.385 inches. For example, the inert ring 222 may have an outer diameter of about 0.465 to 0.655 inches. However, alternate embodiments of may have an outer diameter of less than 0.465 inches or greater than 0.655 inches. For example, the bore 248 of the inert ring 222 may have a diameter of about 0.175 to 0.375 inches. However, alternate embodiments may have a diameter of less than 0.175 inches or greater than 0.375 inches.

In one or more embodiments, the inert ring 222 may be manufactured from any suitable material, including but not limited to, polymers, metals, metal alloys, etc., or from any combination of suitable materials. For example, the inert ring 222 may be manufactured from may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, the inert ring 222 may be manufactured from an underdamped material, a material having a Q factor greater than 0.5, a metal alloy in an annealed condition, a titanium alloy in an annealed condition, or from Ti-6Al-4V extra-low interstitials in an annealed condition.

In an exemplary embodiment, each electrode 220 is generally ring-shaped and includes a distal end surface 250, and proximal end surface 252, a generally annular outer surface 254, and a bore 256. One or more of the electrodes may include leads 258 that operatively connect to the control system 14 via the electrical connection 30 of the connection assembly 16 (FIG. 1). The dimensions of the transducer 218 are predetermined to achieve the proper connection between components. For example, the electrode 220 may have a thickness of about 0.700 to 0.900 inches. However, alternate embodiments may have a thickness of less than 0.700 inches or greater than 0.900 inches. For example, the electrode 220 may have an outer diameter of about 0.465 to 0.655 inches. However, alternate embodiments of may have an outer diameter of less than 0.465 inches or greater than 0.655 inches. For example, the bore 256 of the electrode 220 may have a diameter of about 0.175 to 0.375 inches. However, alternate embodiments may have a diameter of less than 0.175 inches or greater than 0.375 inches. One or more of the electrodes 220 may be manufactured from aluminum, an aluminum alloy, silver, a silver alloy, copper, a copper alloy, gold, a gold alloy, platinum, a platinum alloy, tin, a tin alloy, palladium, a palladium alloy, nickel, a nickel alloy, beryllium, a beryllium alloy, tungsten, a tungsten alloy, a steel, chromium, a chromium alloy, titanium, a titanium alloy, and the like.

In an exemplary embodiment, the connector block 202 is a generally cylindrical component having a distal end 260 configured to detachably connect with the connection assembly 16 and a proximal end 262 configured to couple with the transducer assembly 210. The outer surfaces 264 of the connector block 202 are configured to receive O-rings that form a hermetic seal with the housing 110 (FIG. 5). An aspiration bore 266 extends through the connector block 202 having an inlet 268 for coupling with the aspiration barb 82 at the distal end 260, and an outlet 270 for coupling with a bore 290 of transducer assembly 210 at the proximal end 262. An irrigation bore 272 extends through the connector block 202 having an inlet 274 for coupling with the irrigation barb 52 at the distal end 260, and an outlet 276 for coupling with the coupling with the irrigation channels 122 at the proximal end 262. The dimensions of the transducer 218 are predetermined to achieve the proper configuration of the standing wave 100, and correspondingly, the position of the nodes 102 and anti-nodes 104.

In one or more embodiments, the connector block 202 may be manufactured from any suitable material, including but not limited to, polymers, metals, metal alloys, etc., or from any combination of suitable materials. For example, the connector block 202 may be manufactured from may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, the connector block 202 may be manufactured from an underdamped material, a material having a Q factor greater than 0.5, a metal alloy in an annealed condition, a titanium alloy in an annealed condition, or from Ti-6Al-4V extra-low interstitials in an annealed condition.

In an exemplary embodiment, the amplifier 206 is a generally cylindrical component having a proximal end 284 configured to detachably connect with the surgical attachment 300 and a distal end 286 configured to couple with the transducer assembly 210 (FIG. 5). The dimensions of the amplifier 206 are predetermined to achieve the proper configuration of the standing wave 100, and correspondingly, the position of the nodes 102 and anti-nodes 104.

In one or more embodiments, the amplifier 206 may be manufactured from any suitable material, including but not limited to, polymers, metals, metal alloys, etc., or from any combination of suitable materials. For example, the amplifier 206 may be manufactured from may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, the amplifier 206 may be manufactured from an underdamped material, a material having a Q factor greater than 0.5, a metal alloy in an annealed condition, a titanium alloy in an annealed condition, or from Ti-6Al-4V extra-low interstitials in an annealed condition.

Although the embodiment of FIGS. 1-14 illustrate a motor 200 having a torsional transducer assembly 210, alternate embodiments may substitute a longitudinal transducer assembly, or any other suitable type of transducer assembly that is capable of providing ultrasonic motion at the working plane 18 of the handpiece 12.

Figure 15:
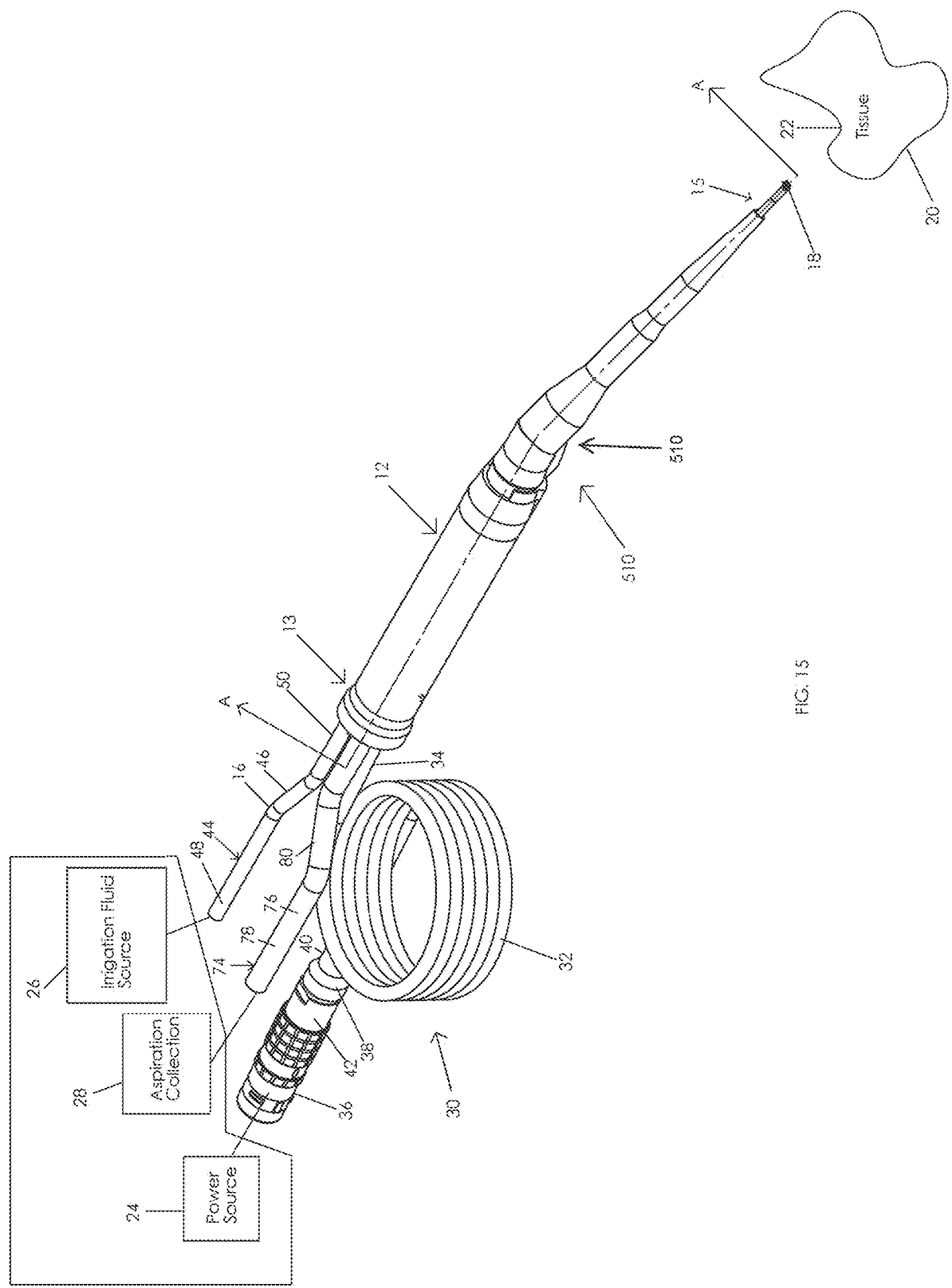
FIG. 15 is a perspective view of an alternate embodiment of an ultrasonic surgical system constructed in accordance with an embodiment.

FIGS. 15-20 illustrate an alternate embodiment of an ultrasonic surgical system. In an exemplary embodiment, the ultrasonic surgical system 10 is similar to the embodiment of FIGS. 1-14, except for an alternate embodiment of an irrigation assembly 510. FIG. 15 is a perspective view of an alternate embodiment of the ultrasonic surgical system 10 constructed in accordance with an embodiment. The surgical handpiece 12 includes an irrigation assembly 510 configured to communicate irrigation fluid from the control system 14 to the working plane 18 of the handpiece 12 through an irrigation path 160.

Figure 16:
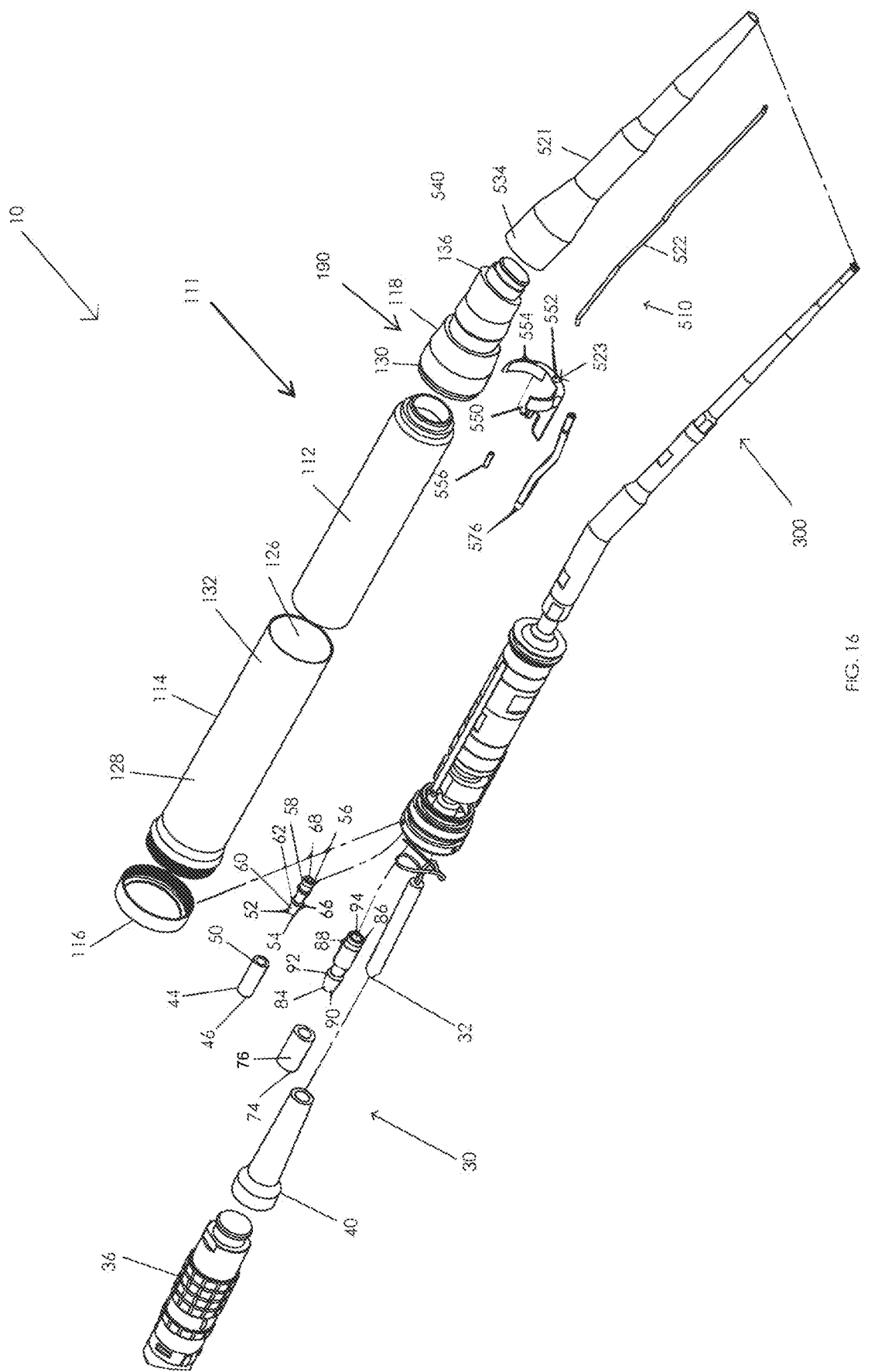
FIG. 16 is a partially exploded perspective view of an alternate embodiment of the ultrasonic surgical handpiece with a housing removed and a connection assembly in accordance with an embodiment.
Figure 17:
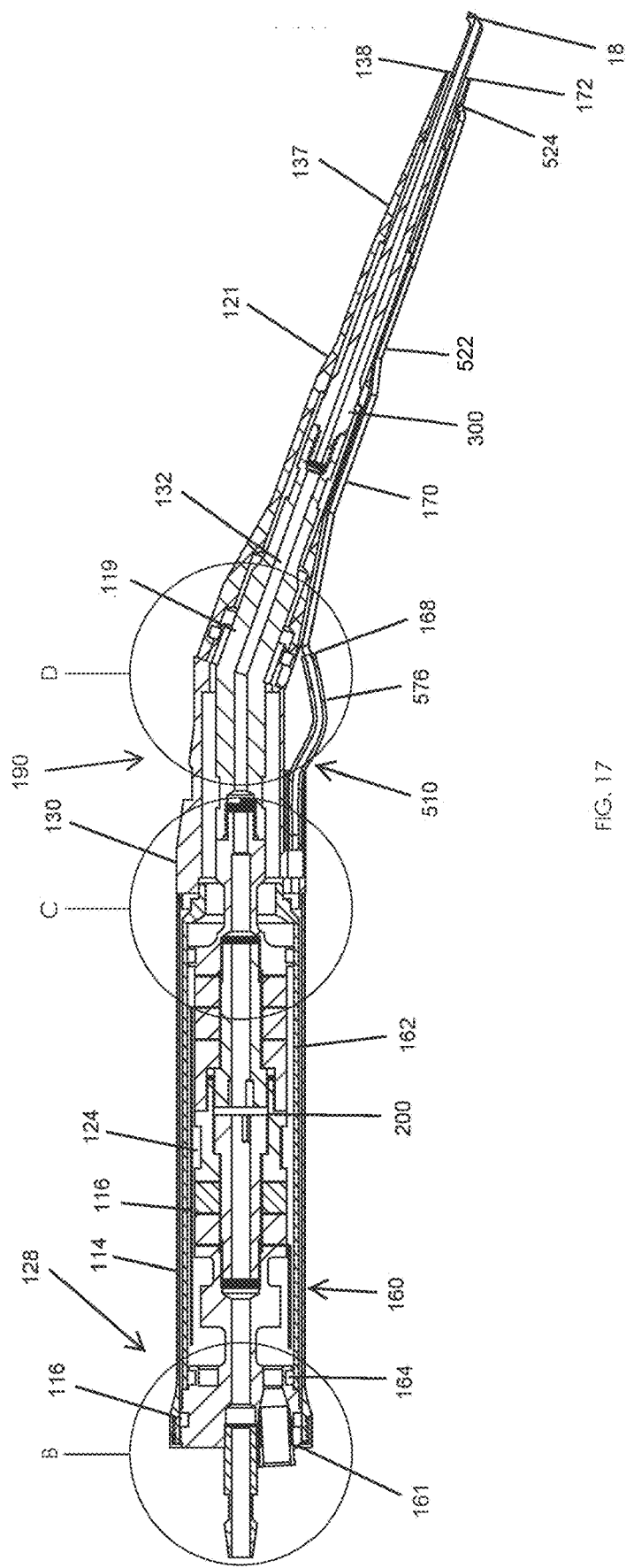
FIG. 17 is a cross-section view of the ultrasonic surgical handpiece taken along section A-A shown in FIG. 15.

FIG. 16 is a partially exploded perspective view of an alternate embodiment of the ultrasonic surgical handpiece with a housing removed and a connection assembly in accordance with an embodiment. FIG. 17 is a cross-section view of the ultrasonic surgical handpiece taken along section A-A shown in FIG. 15. In an exemplary embodiment, the irrigation assembly 510 includes the housing 111 having an inner housing member 112, an outer housing member 114, a collar 116, a nose cone 118, an irrigation member sleeve 521, an irrigation connector, 523, a bypass tube 576, and an irrigation tube 522, that detachably assemble to receive the motor 200 and the surgical attachment 300 and define an irrigation path 160 that communicates irrigation fluid from the irrigation connection 44 to the working plane 18. The irrigation path 160 includes an inlet 161, an inlet channel 164, an intermediate channel 162, a bypass channel 168, an outlet channel 170, and an outlet 172.

Figure 18:
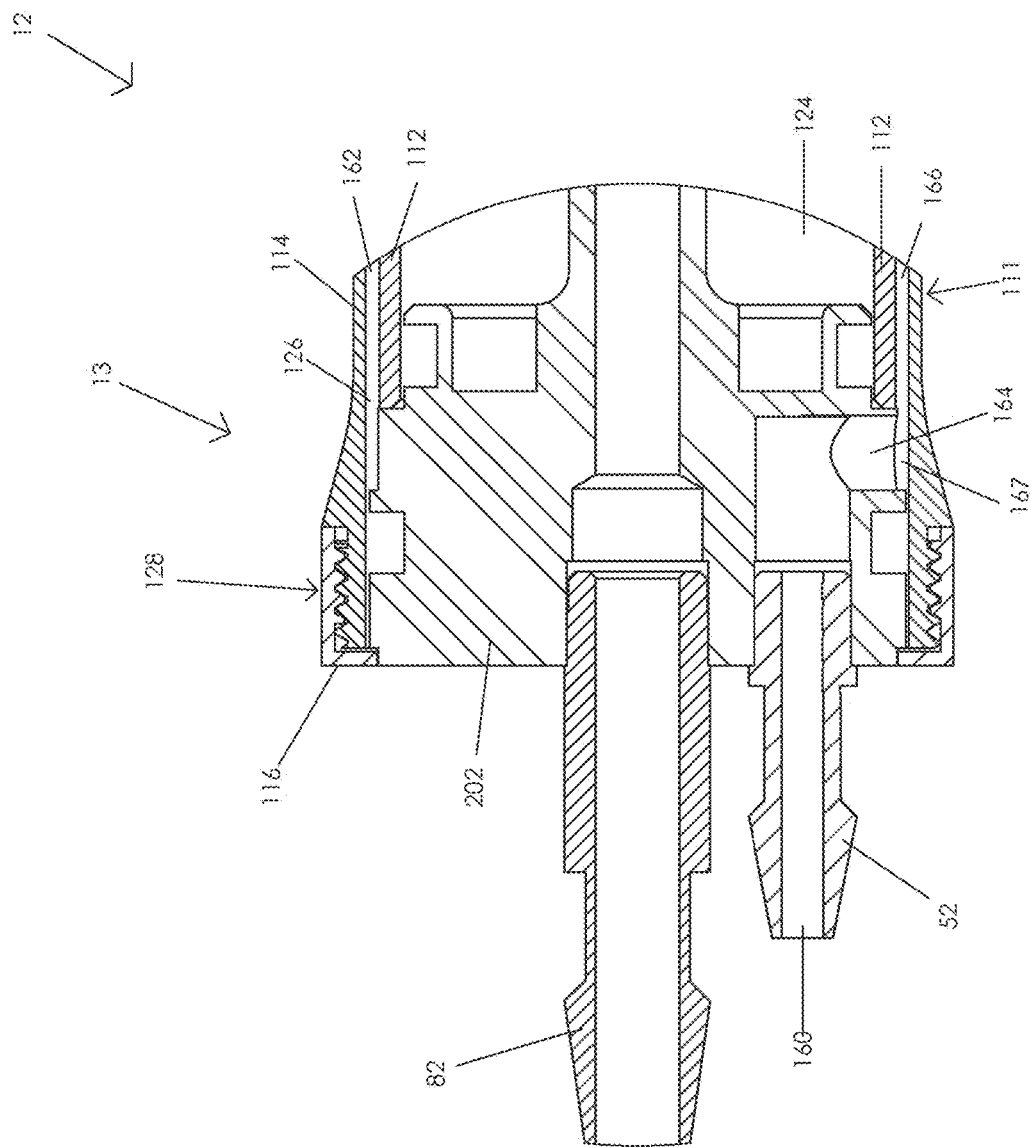
FIG. 18 is an enlarged partial cross-section view of the ultrasonic handpiece taken at section B shown in FIG. 17.
Figure 19:
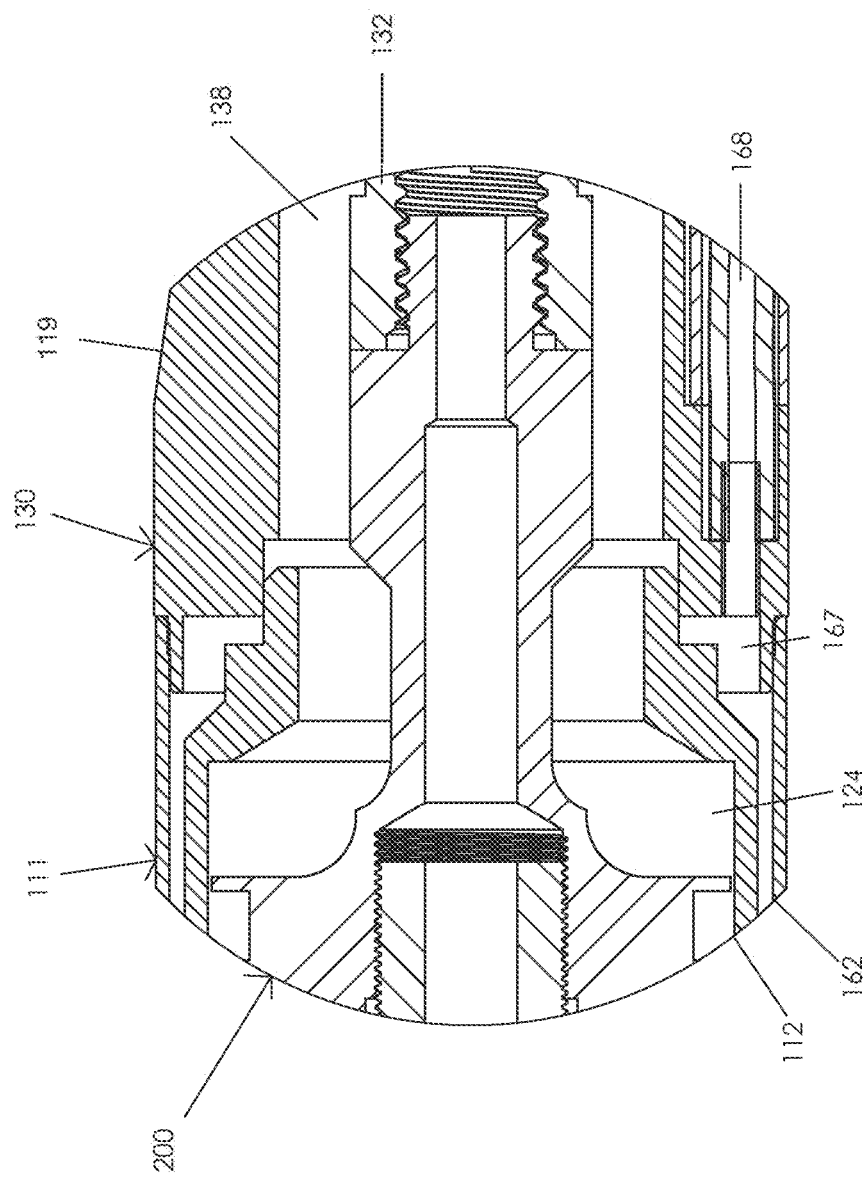
FIG. 19 is an enlarged partial cross-section view of the ultrasonic handpiece taken at section C shown in FIG. 17.

FIG. 18 is an enlarged partial cross-section view of the ultrasonic handpiece taken at section B shown in FIG. 17. FIG. 19 is an enlarged partial cross-section view of the ultrasonic handpiece taken at section C shown in FIG. 17. In an exemplary embodiment, the irrigation path 160 includes the inlet channel 164 at the distal end 13 of the handpiece 12 configured to operatively connect the irrigation connection 44 to the intermediate channel 162 of the housing 111. For example, the inlet channel 164 may extend through the irrigation barb 52 and a connector block 202.

In an exemplary embodiment, the intermediate channel 162 extends through the length of the housing 111 to operatively connect to the bypass channel 168 (FIG. 19). For example, the generally cylindrical inner housing member 112 includes a cavity or bore 124 configured to receive the motor 200 (FIG. 5). The generally cylindrical outer housing member 114 includes a bore 126 configured to receive the inner housing member 112 and motor 200 and defines the generally annular intermediate channel 162 between an outer surface of the inner housing member 112 and an inner surface of the outer housing member 114. The intermediate channel 162 may define annular grooves 167 at each end. In operation, the irrigation fluid flows through the intermediate channel 162 without any physical contact with the motor 200. However, the irrigation fluid may provide cooling to the motor 200 as it flows through the intermediate channel 162 by receiving heat from the motor 200 by thermal conduction and/or convention through the inner housing member 112. The collar 116 detachably couples with a distal end 128 of the outer housing member 114, such as with a threaded connection. The nosecone 118 includes a distal end 130 configured to detachably couple, such as with a threaded connection, with a proximal end 132 of the outer hosing member 126. The nosecone 118 includes a bore 119 configured to receive at least a portion of the surgical attachment 300, such as an angled adaptor 302.

FIG. 20 is an enlarged partial cross-section view of the ultrasonic handpiece taken at section D shown in FIG. 17. In an exemplary embodiment, the bypass channel 168 is configured to operatively connect the intermediate channel 162 with the outlet channel 170. For example, the nosecone 118 may include a bypass outlet 174 with a bypass tube 576 extending from the bypass outlet 174 a bypass inlet 178 of the irrigation member sleeve 121. The irrigation tube 522 may engage with the bypass inlet 178 and/or bypass outlet 174 in any suitable manner. For example, the bypass tube 176 may detachably connect to the bypass inlet 178 and/or bypass outlet 174 using a connector 523, such as a snap-fit type connector. Alternatively, the bypass tube 176 may attach to the bypass inlet 178 and/or bypass outlet 174 using an adhesive, welding, fastener, or the like. In the exemplary embodiment, the bypass tube 176 comprises a flexible material, such as a polymer. However, any suitable material can be used, including, but not limited to metals, metal alloys, etc., or from any combination of suitable materials.

In an exemplary embodiment, the connector 523 includes a base member 550 having a channel 552 that extend longitudinally from a proximate end to a distal end. The proximate end of the channel 552 is configured to operatively connect to the intermediate channel 162 and the distal end of the channel 552 is configured to operatively connect to the bypass tube 576. The connector 523 includes a generally semi-annular retainer member 554 that is configured for detachable connection to the nosecone 118. The connector 523 may also include a tube 556 disposed in the proximal end of the channel 552 to operatively connect between the intermediate channel 162 and the channel 552.

The irrigation member sleeve 521 includes a distal end 534 configured to detachably couple, such as with a threaded connection or a snap-fit type connection, with a proximal end 136 of the nosecone 118 and includes a bore 540 configured to receive a portion of the surgical attachment 300 (FIG. 6). The irrigation member sleeve 521 includes the irrigation tube 522 positioned longitudinally along the outer surface so that the irrigation tube 522 operatively connects the intermediate channel 162 to the outlet 172. For example, the distal end of the irrigation tube 522 may operatively connect to a throughhole 524 of the irrigation member sleeve 521 located proximate to the outlet 138. The outlet 138 is configured to direct irrigation fluid to the working plane 18 and surgical site 22. The irrigation member sleeve 121 may be comprised of any suitable material, including but limited to a heat-shrink material, a tape material, a liquid polymer dip material, and the like.

In operation, the irrigation fluid flows through the irrigation path 160 without contact with an operational portion 190 of the surgical attachment 300. In the exemplary embodiment, the operational portion of the surgical attachment 300 includes the portion disposed between the distal end 308 of the surgical attachment 300 to an interface 192 proximate with the outlet 138. In this way, the irrigation fluid is separated from contact with the operational portion 190 of the surgical attachment so as not to dampen the motion.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

This written description uses examples to disclose several embodiments of the subject matter set forth herein, including the best mode, and also to enable a person of ordinary skill in the art to practice the embodiments of disclosed subject matter, including making and using the devices or systems and performing the methods. The patentable scope of the subject matter described herein is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, communication unit, control system, etc) may be implemented in a single piece of hardware (for example, a general-purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

Since certain changes may be made in the above-described systems and methods, without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

Changes can be made in the above constructions without departing from the scope of the disclosure, it is intended that all matter contained in the above description or shown in the accompanying drawings shall be interpreted as illustrative and not in a limiting sense.

What is claimed is:

1. An ultrasonic surgical handpiece, comprising:
a motor having a transducer assembly along a central axis of the surgical handpiece, the motor being configured for operative connection to a power source;

a surgical attachment having a first end detachably connected to the motor and a second end defining a working plane for engagement with biological tissue;

a housing surrounding the motor and the surgical attachment along the central axis, wherein the housing comprises a cavity configured to receive the motor and the surgical attachment; and an irrigation path configured to communicate irrigation fluid, the irrigation path having an inlet proximate to the housing and operatively connected to an irrigation fluid source, and the irrigation path having an outlet proximate to the working plane, wherein the irrigation path comprises a bypass channel configured to communicate the irrigation fluid to the working plane via the outlet, the bypass channel located outside of the housing, wherein the irrigation path separates the irrigation fluid from an operational portion of the surgical attachment.

2. The ultrasonic surgical handpiece of claim 1, wherein at least a portion of the irrigation path is proximate to the motor for thermal communication between the motor and the irrigation fluid.

3. The ultrasonic surgical handpiece of claim 1, the irrigation path further comprising:
an intermediate channel extending through at least a portion of the housing, the intermediate channel operatively connected to the inlet; and
the bypass channel operatively connected to the intermediate channel and the outlet.

4. The ultrasonic surgical handpiece of claim 3, wherein the irrigation path further comprises an outlet channel downstream of the bypass channel, the outlet channel proximate to the working plane.

5. The ultrasonic surgical handpiece of claim 1, further comprising, an irrigation assembly configured to communicate the irrigation fluid through the irrigation path to the working plane.

6. The ultrasonic surgical handpiece of claim 5, the irrigation assembly further comprising a collar detachably connected to the housing.

7. The ultrasonic surgical handpiece of claim 5, the irrigation assembly further comprising a nose cone detachably connected to the housing, the nose cone having a bypass tube forming the bypass channel.

8. The ultrasonic surgical handpiece of claim 5, the housing further comprising:
an irrigation member sleeve having an irrigation tube configured to communicate the irrigation fluid to the outlet.

9. The ultrasonic surgical handpiece of claim 5, the irrigation assembly further comprising:
an irrigation member having an outer surface with one or more grooves, and a bore configured to receive the surgical attachment; and
an irrigation sleeve surrounding the outer surface of the irrigation member forming one or more outlet channels configured to communicate the irrigation fluid to the outlet.

10. The ultrasonic surgical handpiece of claim 1, the surgical attachment wherein the working plane correlates with an anti-node of a standing wave.

11. The ultrasonic surgical handpiece of claim 1, wherein the irrigation path includes an intermediate channel between the inlet and the bypass channel and an outlet channel between the bypass channel and the outlet.

12. The ultrasonic surgical handpiece of claim 1, wherein the irrigation path comprises a bypass tube forming the bypass channel to bypass the operational portion of the surgical attachment.

13. The ultrasonic surgical handpiece of claim 1, wherein the irrigation path comprises a bypass tube forming the bypass channel to bypass the operational portion of the surgical attachment, the bypass tube being received in a groove formed in an exterior of the housing.

14. The ultrasonic surgical handpiece of claim 1, wherein the housing comprises a housing member holding the motor, a nose cone attached to the housing member, and an irrigation member sleeve extending from the nose cone to the working plane, the irrigation path extending along an interior of the housing member and an interior of the irrigation member sleeve, the irrigation path further extending along an exterior of the nose cone between the housing member and the irrigation member sleeve.

15. The ultrasonic surgical handpiece of claim 14, wherein the irrigation path extends along a portion of the irrigation member sleeve before the irrigation path transitions into the interior of the irrigation member sleeve.

16. An ultrasonic surgical handpiece, comprising:
a motor having a transducer assembly along a central axis of the surgical handpiece, the motor being configured for operative connection to a power source;
a surgical attachment having a first end detachably connected to the motor and a second end defining a working plane for engagement with biological tissue; and
an irrigation assembly having a housing, wherein the housing comprises a cavity configured to receive the motor and the surgical attachment, the irrigation assembly defining an irrigation path configured to communicate irrigation fluid, the irrigation path having an inlet proximate to the housing and operatively connected to an irrigation fluid source, and the irrigation path having an outlet proximate to the working plane, wherein the irrigation path comprises a bypass channel configured to communicate the irrigation fluid to the working plane via the outlet, the bypass channel located outside of the housing, wherein the irrigation path separates from the cavity of the housing outside of the housing separating the irrigation fluid from an operational portion of the surgical attachment.

17. The ultrasonic surgical handpiece of claim 16, wherein at least a portion of the irrigation path is proximate to the motor for thermal communication between the motor and the irrigation fluid.

18. The ultrasonic surgical handpiece of claim 16, the irrigation path further comprising:
an intermediate channel extending through at least a portion of the housing, the intermediate channel operatively connected to the inlet; and
the bypass channel operatively connected to the intermediate channel and the outlet.

19. The ultrasonic surgical handpiece of claim 18, wherein the irrigation path further comprises an outlet channel downstream of the bypass channel, the outlet channel proximate to the working plane.

20. The ultrasonic surgical handpiece of claim 16, wherein the irrigation path further comprises a bypass tube forming the bypass channel, the irrigation path further comprising an intermediate channel between the inlet and the bypass channel and an outlet channel between the bypass channel and the outlet to communicate the irrigation fluid through the irrigation path from the inlet to the outlet at the working plane.

21. The ultrasonic surgical handpiece of claim 16, the irrigation assembly further comprising:
an irrigation member having an outer surface with one or more grooves, and a bore configured to receive the surgical attachment; and
an irrigation sleeve surrounding the outer surface of the irrigation member forming one or more outlet channels configured to communicate the irrigation fluid to the outlet.

22. The ultrasonic surgical handpiece of claim 16, the irrigation assembly further comprising:
an irrigation member sleeve having an irrigation tube configured to communicate the irrigation fluid to the outlet.

23. The ultrasonic surgical handpiece of claim 16, the surgical attachment wherein the working plane correlates with an anti-node of a standing wave.

24. The ultrasonic surgical handpiece of claim 16, wherein the irrigation path includes an intermediate channel between the inlet and the bypass channel and an outlet channel between the bypass channel and the outlet.

25. The ultrasonic surgical handpiece of claim 16, wherein the irrigation path includes a bypass tube forming the bypass channel to bypass the operational portion of the surgical attachment.

26. The ultrasonic surgical handpiece of claim 16, wherein the irrigation path includes a bypass tube forming the bypass channel to bypass the operation portion of the surgical attachment, the bypass tube being received in a groove formed in an exterior of the housing.

27. The ultrasonic surgical handpiece of claim 16, wherein the housing includes a housing member holding the motor, a nose cone attached to the housing member, and an irrigation member sleeve extending from the nose cone to the working plane, the irrigation path extending along an interior of the housing member and an interior of the irrigation member sleeve, the irrigation path further extending along an exterior of the nose cone between the housing member and the irrigation member sleeve.

28. The ultrasonic surgical handpiece of claim 27, wherein the irrigation path extends along a portion of the irrigation member sleeve before the irrigation path transitions into an interior of the irrigation member sleeve.

29. A method of irrigating a surgical handpiece, comprising:
providing a motor having a transducer assembly along a central axis of the surgical handpiece, the motor being configured for operative connection to a power source;
providing a surgical attachment having a first end detachably connected to the motor and a second end defining a working plane for engagement with biological tissue;
providing a housing surrounding the motor and the surgical attachment along the central axis, wherein the housing comprises a cavity configured to receive the motor and the surgical attachment;
providing an irrigation path, the irrigation path having an inlet proximate the housing operatively connected to an irrigation fluid source, and the irrigation path having an outlet proximate to the working plane, wherein the irrigation path comprises a bypass channel configured to communicate the irrigation fluid to the working plane via the outlet, the bypass channel located outside of the housing, wherein the irrigation path separates the irrigation fluid from an operational portion of the surgical attachment; and
communicating the irrigation fluid through the irrigation path.

30. The method of claim 29, wherein said providing an irrigation path comprises an intermediate channel between the inlet and the bypass channel and an outlet channel between the bypass channel and the outlet.

\* \* \* \* \*